US010086057B2

(12) United States Patent
Marconi et al.

(10) Patent No.: US 10,086,057 B2
(45) Date of Patent: Oct. 2, 2018

(54) STAGE SPECIFIC DIAGNOSTIC ANTIGENS, ASSAY AND VACCINE FOR LYME DISEASE

(71) Applicant: Virginia Commonwealth University, Richmond, VA (US)

(72) Inventors: Richard T. Marconi, Richmond, VA (US); Lee D. Oliver, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 15/517,179

(22) PCT Filed: Oct. 8, 2015

(86) PCT No.: PCT/US2015/054690

§ 371 (c)(1),
(2) Date: Apr. 6, 2017

(87) PCT Pub. No.: WO2016/057793

PCT Pub. Date: Apr. 14, 2016

(65) Prior Publication Data

US 2017/0252422 A1 Sep. 7, 2017

Related U.S. Application Data

(60) Provisional application No. 62/199,084, filed on Jul. 30, 2015, provisional application No. 62/061,276, filed on Oct. 8, 2014.

(51) Int. Cl.

| | |
|---|---|
| ***C12Q 1/68*** | (2018.01) |
| ***A61K 39/02*** | (2006.01) |
| ***C07K 14/20*** | (2006.01) |
| ***C12Q 1/04*** | (2006.01) |
| ***G01N 33/569*** | (2006.01) |
| ***C07K 14/435*** | (2006.01) |
| ***C12P 19/34*** | (2006.01) |

(52) U.S. Cl.

CPC .......... *A61K 39/0225* (2013.01); *C07K 14/20* (2013.01); *C07K 14/435* (2013.01); *C12P 19/34* (2013.01); *C12Q 1/04* (2013.01); *C12Q 1/68* (2013.01); *G01N 33/569* (2013.01); *G01N 33/56911* (2013.01); *C07K 2319/02* (2013.01); *G01N 2333/20* (2013.01); *Y02A 50/401* (2018.01); *Y02A 50/57* (2018.01)

(58) Field of Classification Search

None

See application file for complete search history.

(56) References Cited

U.S. PATENT DOCUMENTS 8,808,705 B2 8/2014 Marconi et al.

FOREIGN PATENT DOCUMENTS

WO 2013/158818 A2 10/2013

*Primary Examiner* — Jennifer E Graser

(74) *Attorney, Agent, or Firm* — W&C IP

(57) ABSTRACT

Stage-specific *Borrelia* antigens for diagnosing, treating and/or preventing Lyme disease are provided. The antigens include chimeric *Borrelia* antigen constructs and mutant recombinant proteins comprising OspC and OspE epitopes, respectively. The antigens are used in multiprotein assays that differentiate early, middle and late stage infection, and/or in vaccine preparations.

6 Claims, 20 Drawing Sheets

Specification includes a Sequence Listing.

```
AKLKGEHTDLGKEGVTKGADELEKLFESVKNLSKAAKEMLTNSVKESEKFAGKLKNEHAS
<-----L5I------><-----------H5I--------------><--------L5H--
LGKKDATKGAKELKDLSDSVESLVKASDDFTKKLQSSHAQLGVAGGATTADELEKLFKSV
------><-------H5H-------><---------L5N---------><----------
ESLAKAAQDALANSVNELTSKKLKEKHTDLGKKDATAAELEKLFESVENLAKAAKEMLSN
---H5N-------------><------L5C-----><----------H5C----------
SNKAFTDKLKSSHAELGIANGAATKGAQELEKLFESVKNLSKAAQETLNNSVKESESFTK
><--------L5M----------><------------H5M-------------><-----
KLSDNQAELGIENATKGAEELVKLSESVAGLLKAAQAILANSVKELTSPVVAESPKKPNN
---L5D--------><-------------------H5D-------------------><-
SGKDGNTSANSADESVKGPNLTEISKKITESNAVVLAVKEIETLLSSIDELATKAIGQKI
------------------------------------------------------------
DANGLGVQANQNGSLLAGAYAISTLITQKLSALNSEDLKEKVAKVKKCSEDFTNKLKNGN
------------------------OspC Type F-------------------------
AQLGLAAATDDNAKAAILKTNGTNDKGAKELKDLSDSVESLVKAAQVMLTNSVKELTSPV
------------------------------------------------------------
VAESPKKP (SEQ ID NO: 1)
------->
```

Figure 1

```
STGFTNKLKSGHAELGPVGGNATKGAKELKDLSESVEALAKAAQAMLTNSSEKFT
<--------L5T----------><--------------H5T---------><----
KKLSESHADIGIQAATKGAEELDKLFKAVENLSKSEEFSTKLKDNHAQLGIQGVT
---L5U---------><----H5U---------><---------L5B------->
KGVEELEKLSGSLESLSSTEFTNKLKSEHAVLGLDNLTKGAAELEKLFKAVENLS
<-----H5B--------><------L5E---------><----------------
KAAQDTLKNAVKELTSPIVAESPKKPSEDFTKKLEGEHAQLGIENVTAAELEKLF
-------H5E---------------><--------L5K---------><------
KAVENLAKAAKEMSEKFAGKLKNEHASLGKKDATKGAKELKDLSDSVESLVKASD
---H5K------><------L5H----------><--------H5H------><-
DFTKKLQSSHAQLGVAGGATTADELEKLFKSVESLAKAAQDALANSVNELTSKKL
-------L5N----------><--------------H5N-------------><--
KEKHTDLGKKDATAAELEKLFESVENLAKAAKEMLSNSNKAFTDKLKSSHAELGI
----L5C------><---------H5C------------><---------L5M----
ANGAATKGAQELEKLFESVKNLSKAAQETLNNSVKENNSGKDGNTSANSADESVK
------><-------------H5M--------------><-------------------
GPNLTEISKKITDSNAVLLAVKQVEALLSSIDEIAAKAIGKKIHQNNGLDTENNH
---------------------------------------------------
NGSLLAGAYAISTLIKQKLDGLKNEGLKEKIDAAKKCSETFTNKLKEKHTDLGKE
-------------------OspC Type A E61Q--------------------
GVTDADAKEAILKTNGTKTKGAEELGKLFESVEVLSKAAKEMLANSVKELTSPVV
---------------------------------------------------
AESPKKP (SEQ ID NO: 2)
------>
```

Figure 2

```
SETFTNKLKEKHTDLGKEGVTKGAEELGKLFESVEVLSKAAKEMLANSVKELTSSEEFST
<-------L5 A---------><--------------H5 A--------------><---
KLKDNHAQLGIQGVTKGVEELEKLSGSLESLSSEDFTKKLEGEHAQLGIENVTAAELEKL
---L5 B--------><------H5 B------><--------L5 K--------><---
FKAVENLAKAAKEMAKLKGEHTDLGKEGVTKGADELEKLFESVKNLSKAAKEMLTNSKES
--H5 K--------><------L5 I-----><-----------H5 I----------><
EKFAGKLKNEHASLGKKDATKGAKELKDLSDSVESLVKASDDFTKKLQSSHAQLGVAGGA
-------L5 H--------><-------H5 H-------><--------L5 N-------
TTADELEKLFKSVESLAKAAQDALANSVNELTSKKLKEKHTDLGKKDATAAELEKLFESV
-><------------H5 N-------------><-----L5 C------><---------
ENLAKAAKEMLSNSNKAFTDKLKSSHAELGIANGAATKGAQELEKLFESVKNLSKAAQET
-H5 C---------><---------L5 M---------><-----------H5 M-----
LNNSVKESESFTKKLSDNQAELGIENATKGAEELVKLSESVAGLLKAAQAILANSVKELT
------><--------L5 D--------><-----------------H5 D---------
SPVVAESPKKP (SEQ ID NO: 3)
><---C10-->
```

Figure 3

SEKFTTKLKDSHAELGIQSVQDKGAKELEELFKSLESLSKAAQAALTNSVKELTNSDKFT

<-----L5 PWa-----><--------------H5 PWa---------------><----

KKLTDSHAQLGAVGGAINDKGAKELKELSESVESLAKAAQAALANSSEAFTKKLKDSNAQ

-----L5 Pli------><-----------H5 Pli---------><------L5 PBes

LGMQNGAATDKGATELGELFKSVESLSKAAQEASVAFTSKLKSSNAQLGVANGNATDKGA

--------><--------H5 PBes-------><--------L5 Pki-------><---

KELKELFESVESLAKAAQAALVNSVQELTNSEAFTNRLKGSHAQLGVAAATDKGAKELKD

-------H5 Pki----------------><------L5 PFim------><--------

LSESVESLAKAAQEALANSVKELTNSEAFTNKLKEKHAELGVNGGDTTDKGVEDLEKLSE

---H5 PFim--------------><----L5 Smar-----------><----------

SVKSLLKAAQAALSNSAAFTKKLQDGHVDLGKTDVTTKGATELEELFKSVEGLVKAAKEA

H5 Smar---------><------L5 HT22------><------H5 HT22------->

SETFTNKLKEKHTDLGKEGVTKGAEELGKLFESVEVLSKAAKEMLANSVKELTSSEDFTK

<-------L5 A---------><--------------H5 A--------------><---

KLEGEHAQLGIENVTAAELEKLFKAVENLAKAAKEMAPVVAESPKKP (SEQ ID NO: 4)

| Clone # | | #m | iAb | FH | SEQ ID NO: |
|---|---|---|---|---|---|
| | aa 16 aa92 | | | | |
| L39wt | LIGACKIHTSYDEQSNGEVKVKKIEFSEFTVKIKNKNNSNNWADLGDLVVRKEKDGIETGLNAGGHSATFFSLEEEE | 0 | + | + | 10 |
| L39-100 | ...........V.................................................K............... | 5 | + | - | 11 |
| L39-75 | ...........V.....V.........................................D................. | 4 | + | - | 12 |
| L39-84 | ............................................................................. | 1 | + | + | 13 |
| L39-9 | ..................................................................L.......... | 1 | + | - | 14 |
| L39-8 | .............................................R............................... | 1 | + | - | 15 |
| L39-103 | ............................................................................. | 3 | + | - | 16 |
| L39-70 | .....................E.......................................K............... | 2 | + | - | 17 |
| L39-67 | ...........................Q....................................A............ | 4 | + | +/- | 18 |
| L39-88 | ............................................................................. | 4 | - | - | 19 |
| L39-72 | ........P...........I..............................................T......... | 5 | + | - | 20 |
| L39-69 | ............................................................................. | 5 | + | - | 21 |
| L39-7 | ...............................N..........................R.................. | 3 | + | - | 22 |
| L39-48 | ............................................................................. | 1 | - | - | 23 |
| L39-37 | .............................I...........C............................V...... | 3 | + | - | 24 |
| L39-90 | ............................................E....I..............R............ | 7 | + | - | 25 |
| L39-51 | .................................................................QL...L...... | 5 | + | - | 26 |

Figure 8

```
         aa93                                                                              aa173               SEQ ID NO:
                                                                                                               (Con't)
L39wt    INNFIKAMTEGGSFKTSLYYGYNDEESDKNVIKNKEIKTKIEKINDTEYITFLGDKINNSAGGDKIAEYAISLEELKRNLK* 0  +  +     10
L39-100  .............................S......V......................C.....................* 5  +  -     11
L39-75   .............................S...................................................* 4  +  -     12
L39-84   .......I.........................................................................* 1  +  +     13
L39-9    .................................................................................* 1  +  -     14
L39-8    .................................................................................* 1  +  -     15
L39-103  .............................S......VR...........................................* 3  +  -     16
L39-70   .................................................................................* 2  +  -     17
L39-67   .............................S......V............................................* 4  +  +/-   18
L39-88   ......P......................S......V.............................V..............* 4  -  -     19
L39-72   .............................S......V............................................* 5  +  -     20
L39-69   .....N..............R...............M............................................* 5  +  -     21
L39-7    .............................................................................S...* 3  +  -     22
L39-48   ..........D.........................................................*              1  -  -     23
L39-37   .................................................................................* 3  +  -     24
L39-90   .............................S......V.........................R......T...........* 7  +  -     25
L39-51   ...........................G................................V....................* 5  +  -     26
```

Figure 8 (continued)

| Clone | aa16 … 105 | #m | iAb | FH | SEQ ID NO: |
|---|---|---|---|---|---|
| N38wt | LIGACKIHTSYDEQSSGEINHTLYDEQSNGELKLKKIEFSKFTVKIKNKDNNSNWTDLGDLVVRKEENGIDTGLNAGGHSATFFSIKESE | 0 | + | + | 27 |
| N38-20 | ...........................................................................I.............. | 4 | - | - | 28 |
| N38-13 | .....................................................................N.........DM......... | 4 | + | - | 29 |
| N38-25 | ................V.............................................................E........... | 3 | - | - | 30 |
| N38-37 | ...........G..................D..........................................S................ | 4 | +- | | 31 |
| N38-7 | ..............I.....R.................................................................T... | 6 | - | - | 32 |
| N38-5 | ...........G.............................I.........K.............................V.......G | 6 | - | - | 33 |
| N38-31 | ................................................TV........................................ | 4 | - | - | 34 |
| N38-32 | S......................................................................................... | 14 | - | - | 35 |

Figure 9

| | aa106 … 186 | | | | | SEQ ID NO: (con't) |
|---|---|---|---|---|---|---|
| BBN38wt | VNNFIKAMTKGGSFKTSLYYGYKYEQSSANGIQNKEIITKIESINGAEHIAFLGDKINNGVGGDKTAEYAIPLEVLKKNL K* | 0 | + | + | | 27 |
| N38-20 | ............................................V........................V.....V.... .* | 4 | - | - | | 28 |
| N38-13 | ...................................................V............................ .* | 4 | + | - | | 29 |
| N38-25 | ........S....................................................................... .* | 3 | - | - | | 30 |
| N38-37 | ............................................................S................... .* | 4 | + | - | | 31 |
| N38-7 | ......T............F.....................................................I...... .* | 6 | - | - | | 32 |
| N38-5 | .......................................................................V........ .* | 6 | - | - | | 33 |
| N38-31 | .......................................................VN....................... .* | 4 | - | - | | 34 |
| N38-32 | ........................................................L.TVW.KI.QLNMQYH* | *14 | - | - | | 35 |

Figure 9 (con't)

```
1   mkkntlsail mtlflfiscn nsgkdgntsa nsadesvkgp nlteiskkit dsnavllavk
        Signal peptide

61  eveallssid eiaakaigkk ihqnngldte nnhngsllag ayaistlikq kldglknegl

121 kekidaakkc setftnklke khtdlgkegv tdadakeail ktngtktkga eelgklfesv
               "loop 5" epitope               "alpha helix 5" epitope

181 evlskaakem lansvkelts pvvaespkkp  (SEQ ID NO: 36)
     ...epitope continued  C10 domain
```

FIGURE 12

```
SEDFTNKLKNGNAQLGLAAATKGAKELKDLSDSVESLVKAAQVMLTNSSTGFTNKLKSGH
<-------lpF---------><-----------hxF-----------><------lpT-

AELGPVGGNATKGAKELKDLSESVEALAKAAQAMLTNSSEKFTKKLSESHADIGIQAATK
----------><----------hxT------------><--------lpU--------><

GAEELDKLFKAVENLSKSTEFTNKLKSEHAVLGLDNLTKGAAELEKLFKAVENLSKAAQD
------hxU-------><--------lpE--------><----------------hxE--

TLKNAVKELTSPIVAESPKKPSETFTNKLKEKHTDLGKEGVTKGAEELGKLFESVEVLSK
--------------------><-------lpA---------><----------hxA----

AAKEMLANSVKELTSSEEFSTKLKDNHAQLGIQGVTKGVEELEKLSGSLESLSSEDFTKK
--------------><------lpB-----------><------hxB------><------

LEGEHAQLGIENVTAAELEKLFKAVENLAKAAKEMAKLKGEHTDLGKEGVTKGADELEKL
--lpK--------><--------hxK--------><-----lpI------><--------

FESVKNLSKAAKEMLTNSVKESEKFAGKLKNEHASLGKKDATKGAKELKDLSDSVESLVK
---hxI--------------><--------lpH--------><-------hxH-------

ASDDFTKKLQSSHAQLGVAGGATTADELEKLFKSVESLAKAAQDALANSVNELTSKKLKE
><---------lpN---------><-------------hxN-------------><----

KHTDLGKKDATAAELEKLFESVENLAKAAKEMLSNSNKAFTDKLKSSHAELGIANGAATK
--lpC-----><----------hxC----------><--------lpM----------><

GAQELEKLFESVKNLSKAAQETLNNSVKESESFTKKLSDNQAELGIENATKGAEELVKLS
------------hxM-------------><--------lpD--------><---------

ESVAGLLKAAQAILANSVKELTSPVVAESPKKPNNSGKDGNTSANSADESVKGPNLTEIS
----------hxD-------------------><--------------------------

KKITESNAVVLAVKEIETLLSSIDELATKAIGQKIDANGLGVQANQNGSLLAGAYAISTL
------------------------------OspC Type F-------------------

ITQKLSALNSEDLKEKVAKVKKCSEDFTNKLKNGNAQLGLAAATDDNAKAAILKTNGTND
------------------------------------------------------------

KGAKELKDLSDSVESLVKAAQVMLTNSVKELTSPVVAESPKKP  (SEQ ID NO:5)
------------------------------------------>
```

Figure 13A

```
SEDFTNKLKNGNAQLGLAAATKGAKELKDLSDSVESLVKAAQVMLTNSSTGFTNKLKSGH
<-------lpF----------><-----------hxF----------><------lpT--

AELGPVGGNATKGAKELKDLSESVEALAKAAQAMLTNSSEKFTKKLSESHADIGIQAATK
-----------><----------hxT-----------><--------lpU--------><

GAEELDKLFKAVENLSKSTEFTNKLKSEHAVLGLDNLTKGAAELEKLFKAVENLSKAAQD
------hxU-------><--------lpE--------><----------------hxE--

TLKNAVKELTSPIVAESPKKPSETFTNKLKEKHTDLGKEGVTKGAEELGKLFESVEVLSK
--------------------><-------lpA---------><----------hxA----

AAKEMLANSVKELTSSEEFSTKLKDNHAQLGIQGVTKGVEELEKLSGSLESLSSEDFTKK
--------------><------lpB----------><------hxB------><------

LEGEHAQLGIENVTAAELEKLFKAVENLAKAAKEM          (SEQ ID NO: 6)
--lpK--------><--------hxK-------->
```

Figure 13B

```
AKLKGEHTDLGKEGVTKGADELEKLFESVKNLSKAAKEMLTNSVKESEKFAGKLKNEHAS
<-----lpI------><-----------hxI--------------><--------lpH--

LGKKDATKGAKELKDLSDSVESLVKASDDFTKKLQSSHAQLGVAGGATTADELEKLFKSV
------><-------hxH-------><---------lpN---------><----------

ESLAKAAQDALANSVNELTSKKLKEKHTDLGKKDATAAELEKLFESVENLAKAAKEMLSN
---hxN-------------><------lpC-----><----------hxC----------

SNKAFTDKLKSSHAELGIANGAATKGAQELEKLFESVKNLSKAAQETLNNSVKESESFTK
><--------lpM----------><------------hxM------------><-----

KLSDNQAELGIENATKGAEELVKLSESVAGLLKAAQAILANSVKELTSPVVAESPKKP
---lpD--------><------------------hxD------------------>
```

(SEQ ID NO: 7)

Figure 13C

```
AKLKGEHTDLGKEGVTKGADELEKLFESVKNLSKAAKEMLTNSVKESEKFAGKLKNEHAS
<-----lpI------><-----------hxI--------------><---------lpH--

LGKKDATKGAKELKDLSDSVESLVKASDDFTKKLQSSHAQLGVAGGATTADELEKLFKSV
------><-------hxH-------><---------lpN---------><----------

ESLAKAAQDALANSVNELTSKKLKEKHTDLGKKDATAAELEKLFESVENLAKAAKEMLSN
---hxN-------------><------lpC-----><----------hxC----------

SNKAFTDKLKSSHAELGIANGAATKGAQELEKLFESVKNLSKAAQETLNNSVKESESFTK
><---------lpM----------><-------------hxM-------------><-----

KLSDNQAELGIENATKGAEELVKLSESVAGLLKAAQAILANSVKELTSPVVAESPKKPST
---lpD--------><-------------------hxD-------------------><-

EEKFNEKGEVSEKIITRADGTRLEYTGIKSDGSGKAKEVLKGYVLEGTLTAEKTTLVVKE
------------------------------------OspA121273------------

GTVTLSKNISKSGEVSVELNDTDSSAATKKTAAWNSGTSTLTITVNSKKTKDLVFTKENT
------------------------------------------------------------

ITVQQYDSNGTKLEGSAVEITKLDEIKNALK          (SEQ ID NO: 8)
------------------------------->
```

Figure 13D

| OspC Type | *Borrelia* species | | | | Geographic Region | | | | | Isolated from | | | | | |
|---|---|---|---|---|---|---|---|---|---|---|---|---|---|---|---|
| | *B. burgdorferi* | *B. garinii* | *B. afzelii* | Other species | North America | Europe | Russia | Asia | Not provided | Human Skin | Human Blood | Human CSF | Other animal | Tick | Not provided |
| **Assigned** | | | | | | | | | | | | | | | |
| A (B31) | 38 | | | | 25 | 9 | | 4 | | 7 | 9 | 6 | 6 | 7 | 3 |
| B (LDP73) | 13 | | | | 6 | 5 | | | 2 | 5 | 1 | 1 | | 4 | 2 |
| D (LDP116) | 3 | | | | 3 | | | | | | 1 | | | 2 | |
| E (N40) | 7 | | | | 7 | | | | | 3 | | | | 4 | |
| F (PAd) | 4 | | | | 4 | | | | | 1 | | | | 3 | |
| H (LDS101) | 3 | | | | 3 | | | | | 2 | | | | 1 | |
| I (HB19) | 7 | | | | 7 | | | | | 3 | 2 | 1 | | 1 | |
| K (LDP74) | 11 | | | | 11 | | | | | 3 | 2 | 1 | | 5 | |
| L (SI1) | 6 | | | | 5 | 1 | | | | | | | 5 | 1 | |
| M (B356) | 3 | | | | 3 | | | | | 1 | | | 2 | | |
| N (LDP63) | 7 | | | | 7 | | | | | 1 | 2 | 1 | 1 | 2 | |
| U (148) | 3 | | | | 3 | | | | | 1 | | | | 2 | |
| OspCt-Smar | | 4 | | | | 4 | | | | | | 1 | | 3 | |
| OspCt-PLi | | 9 | | | | 9 | | | | 5 | 1 | 3 | | | |
| OspCt-H13 | | 3 | | | | 3 | | | | 1 | | 1 | | 1 | |
| OspCt-PFiM | | 6 | | | | 6 | | | | 1 | | 3 | | 2 | |
| OspCt-PMit | | 3 | | | | 3 | | | | 1 | | 1 | | 1 | |
| OspCt-PKi | | 5 | | | | 5 | | | | 3 | | 2 | | | |
| OspCt-PBes | | 7 | | | | 6 | | 1 | | 3 | | 3 | | 1 | |
| OspCt-HT22 | | 4 | | | | | 3 | 1 | | | | | | 4 | |
| OspCt-Pko | | | 11 | | | 7 | | 4 | | 5 | | 1 | 2 | 3 | |
| OspCt-PLj7 | | | 6 | | | 5 | | | 1 | 3 | 1 | | | 1 | 1 |
| OspCt-VS461 | | | 3 | | | 2 | | | 1 | 1 | | | | 1 | 1 |
| OspCt-DK15 | | | 3 | | | 1 | | 2 | | 1 | | | | 2 | |
| OspCt-HT25 | | | 4 | | | | 1 | 3 | | | | | | 4 | |
| OspCt-72a | 4 | | | | 4 | | | | | 1 | | | 1 | 2 | |
| OspCt-Szid | 3 | | | | | 3 | | | | 1 | | 1 | | 1 | |
| OspCt-PHez | | 5 | | | | 5 | | | | | | 4 | | 1 | |
| OspCt-PWa | | 17 | | | | 17 | | | | 1 | | 16 | | | |
| **Unassigned** | | | | | | | | | | | | | | | |
| *B. burgdorferi* | 8 | | | | 6 | 1 | 1 | | | 1 | 1 | | 1 | 5 | |
| *B. garinii* | | 22 | | | | 7 | 4 | 10 | 1 | 4 | | 2 | | 15 | 1 |
| *B. afzelii* | | | 21 | | | 10 | 9 | 1 | 1 | 7 | | | 3 | 10 | 1 |
| *B. bissettii* | | | | 8 | 8 | | | | | | | | 6 | 2 | |
| *B. japonica* | | | | 1 | | | | 1 | | | | | | | 1 |
| *B. andersonii* | | | | 6 | 6 | | | | | | | | 1 | 5 | |
| *B. tanukii* | | | | 1 | | | | 1 | | | | | 1 | | |
| *B. valaisiana* | | | | 8 | | 4 | | 4 | | | | | 3 | 5 | |
| *B.* species | | | | 3 | 3 | | | | | | | | 1 | 2 | |
| **Totals** | 120 | 85 | 48 | 27 | 111 | 113 | 18 | 32 | 6 | 66 | 20 | 48 | 33 | 103 | 10 |

Figure 14

| Number of Dogs Tested | A12CF EU | BBN38 EU | BBL39-9 EU | Total EU |
|---|---|---|---|---|
| 78 | 632.00 ± 80.43 | 620.64 ± 81.26 | 642.44 ± 115.43 | 1895.13 ± 203.67 |
| Can Pos | 3077.00 | 2660.00 | 1430.00 | 7167.00 |

Figure 15

| Dog ID #-Day PI | A12CF EU | BBN38 EU | BBL39-9 EU | Total EU | Total EU x DF | 1.2 cutoff | Immuno-blot | SNAP 4DX |
|---|---|---|---|---|---|---|---|---|
| Can Pool Neg | 5.00 | 5.00 | 5.00 | 15.00 | 1500.00 | neg | neg | neg |
| Can Pos | 28.70 | 31.73 | 46.10 | 106.53 | 10653.33 | pos | pos | pos |
| Can1 | 10.10 | 9.87 | 16.77 | 36.73 | 3673.33 | pos | neg | wp |
| Can2 | 30.47 | 20.97 | 32.63 | 84.07 | 8406.67 | pos | pos | pos |
| Can3 | 8.33 | 7.30 | 16.67 | 32.30 | 3230.00 | pos | pos | wp |
| Can4 | 6.27 | 8.10 | 7.00 | 21.37 | 2136.67 | pos | pos | pos |
| Can5 | 8.47 | 24.30 | 60.43 | 93.20 | 9320.00 | pos | pos | wp |
| Can6 | 7.00 | 9.60 | 12.87 | 29.47 | 2946.67 | pos | pos | pos |
| Can7 | 8.23 | 22.87 | 7.93 | 39.03 | 3903.33 | pos | pos | pos |
| Can8 | 16.33 | 6.90 | 38.80 | 62.03 | 6203.33 | pos | wk | pos |
| Can9 | 10.77 | 29.07 | 37.73 | 77.57 | 7756.67 | pos | pos | pos |
| Can10 | 7.97 | 12.00 | 25.10 | 45.07 | 4506.67 | pos | pos | pos |
| Can11 | 8.43 | 8.67 | 26.80 | 43.90 | 4390.00 | pos | pos | pos |
| Can12 | 7.37 | 7.97 | 13.70 | 29.03 | 2903.33 | pos | wk | pos |
| Can13 | 19.10 | 29.57 | 39.90 | 88.57 | 8856.67 | pos | pos | pos |
| Can14 | 6.80 | 8.47 | 16.57 | 31.83 | 3183.33 | pos | wk | pos |
| Can15 | 8.55 | 7.33 | 18.07 | 33.95 | 3395.00 | pos | neg | wp |
| Can16 | 11.90 | 11.95 | 47.90 | 71.75 | 7175.00 | pos | pos | pos |
| Can17 | 6.77 | 8.43 | 23.57 | 38.77 | 3876.67 | pos | pos | wp |
| Can18 | 9.53 | 6.77 | 17.03 | 33.33 | 3333.33 | pos | pos | wp |
| Can19 | 8.17 | 10.47 | 31.87 | 50.50 | 5050.00 | pos | pos | pos |
| Can20 | 6.97 | 14.97 | 42.00 | 63.93 | 6393.33 | pos | pos | pos |
| Can21 | 6.33 | 7.53 | 25.07 | 38.93 | 3893.33 | pos | pos | pos |
| Can22 | 17.93 | 9.13 | 14.17 | 41.23 | 4123.33 | pos | pos | pos |
| Can23 | 36.00 | 21.73 | 33.00 | 90.73 | 9073.33 | pos | pos | pos |
| Can24 | 35.97 | 13.27 | 31.97 | 81.20 | 8120.00 | pos | pos | pos |
| Can25 | 10.83 | 12.93 | 6.97 | 30.73 | 3073.33 | pos | pos | pos |
| Can26 | 10.93 | 15.63 | 8.90 | 35.47 | 3546.67 | pos | pos | pos |
| Can27 | 8.85 | 9.20 | 49.70 | 67.75 | 6775.00 | pos | pos | pos |
| Can28 | 31.13 | 16.80 | 12.95 | 60.88 | 6088.33 | pos | pos | pos |
| Can29 | 25.60 | 12.97 | 10.83 | 49.40 | 4940.00 | pos | pos | pos |
| Can30 | 15.03 | 14.97 | 9.83 | 39.83 | 3983.33 | pos | wk | pos |
| Can31 | 43.23 | 8.70 | 16.70 | 68.63 | 6863.33 | pos | pos | pos |
| Can32 | 12.25 | 16.23 | 39.20 | 67.68 | 6768.33 | pos | pos | pos |
| Can33 | 18.83 | 24.07 | 8.13 | 51.03 | 5103.33 | pos | pos | pos |
| Can34 | 10.07 | 17.47 | 11.90 | 39.43 | 3943.33 | pos | pos | pos |
| Can35 | 33.93 | 9.03 | 33.00 | 75.97 | 7596.67 | pos | pos | wp |
| Can36 | 33.20 | 12.57 | 31.97 | 77.73 | 7773.33 | pos | pos | pos |
| Can37 | 9.67 | 8.87 | 6.97 | 25.50 | 2550.00 | pos | neg | wp |
| Can38 | 9.27 | 10.60 | 8.90 | 28.77 | 2876.67 | pos | pos | pos |
| Can39 | 12.70 | 34.83 | 49.70 | 97.23 | 9723.33 | pos | pos | pos |
| Can40 | 11.30 | 8.20 | 12.95 | 32.45 | 3245.00 | pos | neg | pos |
| Can41 | 16.55 | 10.80 | 10.83 | 38.18 | 3818.33 | pos | pos | pos |
| Can42 | 10.37 | 8.63 | 9.83 | 28.83 | 2883.33 | pos | pos | pos |
| Can43 | 15.83 | 23.73 | 16.70 | 56.27 | 5626.67 | pos | pos | pos |
| Can44 | 13.23 | 12.47 | 39.20 | 64.90 | 6490.00 | pos | pos | pos |
| Can45 | 8.27 | 7.87 | 8.13 | 24.27 | 2426.67 | pos | pos | wp |
| Can46 | 9.70 | 7.40 | 11.90 | 29.00 | 2900.00 | pos | wk | pos |
| Can47 | 30.20 | 8.10 | 30.13 | 68.43 | 6843.33 | pos | pos | pos |
| Can48 | 8.73 | 9.55 | 10.30 | 28.58 | 2858.33 | pos | wk | pos |
| Can49 | 11.13 | 10.23 | 18.27 | 39.63 | 3963.33 | pos | neg | pos |
| Can51 | 7.10 | 9.30 | 7.40 | 23.80 | 2380.00 | neg | neg | neg |
| Can53 | 8.20 | 8.50 | 13.10 | 29.80 | 2980.00 | pos | neg | neg |
| Can54 | 11.20 | 10.00 | 7.50 | 28.70 | 2870.00 | pos | pos | neg |

Figure 16

STAGE SPECIFIC DIAGNOSTIC ANTIGENS, ASSAY AND VACCINE FOR LYME DISEASE

CROSS-REFERENCE TO RELATED APPLICATIONS

This application claims benefit of U.S. provisional patent applications 62/061,276, filed Oct. 8, 2014, and 62/199,084, filed Jul. 30, 2015, the complete contents of each of which are hereby incorporated by reference.

STATEMENT OF FEDERALLY SPONSORED RESEARCH AND DEVELOPMENT

This invention was made with government support under grant numbers 5RO1A1067746 and 5RO1A1037787 awarded by the National Institutes of Health. The United States government has certain rights in the invention.

SEQUENCE LISTING

This application includes as the Sequence Listing the complete contents of the accompanying text file “Sequence.txt”, created Oct. 5, 2015, containing 75,672 bytes, hereby incorporated by reference.

BACKGROUND OF THE INVENTION

Field of the Invention

The invention generally relates to stage-specific *Borrelia* antigens for diagnosing, treating and/or preventing Lyme disease. In particular, the invention provides chimeric and recombinant mutant *Borrelia* antigen constructs, as well as multiprotein assays and vaccine preparations utilizing the constructs.

Background

Lyme disease, also known as Lyme borreliosis, is an infectious disease caused by several bacterial species belonging to the *Borrelia burgdorferi* sensu lato complex. This complex of bacteria consists of approximately 15 species. The word approximately is used in the previous sentence because the species status of some in the group has not yet been fully agreed upon by the research community. The major species that are associated with human and veterinary infections are *B. burgdorferi, B. garinii, B. afzelii*, and *B. bavariensis*. Collectively all bacterial species in the *B. burgdorferi* sensu lato complex are commonly referred to as the Lyme disease spirochetes. The Lyme disease spirochetes are transmitted to humans and animals through the bite of infected ticks of the *Ixodes* genus. Lyme disease is now the most common arthropod borne disease in the Northern Hemisphere. It is estimated to affect 300,000 to 600,000 people a year in the United States with similar numbers in Europe. While Lyme disease also occurs in parts of Asia the actual number of cases is not well defined due to difficulties in tracking cases. In North America, the primary species that causes disease in humans and companion animals is *Borrelia burgdorferi* (sometimes referred to as *B. burgdorferi* sensu stricto), while in Europe and Asia, at least four species cause Lyme disease (*B. burgdorferi, B. afzelii B. bavariensis* and *B. garinii*). Diagnosis of Lyme disease remains a controversial and difficult area. Currently, diagnosis is made based upon a combination of symptoms, history of tick exposure, and serological assays that test for antibodies to the bacteria in the blood.

Current diagnostic tests for Lyme disease are considered by public health authorities and the medical and research communities as being highly unreliable. In addition, the most commonly used commercially available tests are not able to detect early infection, distinguish between prior and active infection, or differentiate early and late stage disease. These are significant disadvantages since the optimal and most effective treatment strategies for early and late stage Lyme disease, particularly in humans, differ. Early stage disease is treated with oral antibiotics while intravenous antibiotics are used by most clinicians to treat late stage infection. Because currently available diagnostics do not distinguish between disease stages, patients with late stage disease are thus frequently subjected to multiple ineffective courses of oral antibiotics before receiving more effective IV treatment.

In addition, antigens currently used in Lyme diagnosis are typically native natural proteins, or peptides derived from those proteins. The proteins used in these assays are derived in most cases from a single strain of Lyme disease spirochete. The tests are not designed to detect the multiple species that can cause disease in humans or animals. In addition, proteins of the Lyme disease spirochetes have been demonstrated to vary considerably in sequence from strain to strain (even of the same species). Hence, the failure to consider this in assay design or use of proteins that are not evolutionary conserved can lead to false negative test results. To restate, few proteins produced by the Lyme disease spirochetes during natural infection meet the criteria of being highly conserved among the multiple species of bacteria that cause Lyme disease worldwide, and current tests do not employ a sufficient number of appropriate antigens to ensure detection of diverse strains.

There is a pressing need in the art to provide accurate diagnostic tests to detect Lyme disease infection. In particular, there is a need to accurately differentiate among different stages of Lyme disease so that appropriate treatment can be administered, and to detect the presence of infection caused by diverse *Borrelia* strains.

SUMMARY OF THE INVENTION

The invention provides chimeric and recombinant antigenic constructs which, when used in the diagnostic assays described herein, differentiate stages of infection with the Lyme disease spirochete. A first construct comprises a chimeric protein that comprises isolated epitopes from multiple different Lyme disease spirochete Outer surface protein C (OspC) variants and detects, in a sample from a subject, anti-OspC antibodies produced early in infection. Additional recombinant constructs comprise genetically modified *Borrelia* OspE proteins (designated as BBL39 and BBN38) and detect anti-OspE antibodies produced during mid to late infection. The term “OspE” is used to collectively refer to BBL39 and BBN38. Where appropriate in this document, the OspE proteins are referred to individually as BBL39 and BBN38. A ratio of the quantities of OspC to OspE Abs measured in the sample permits differentiation of early, middle and late stage Lyme disease. The diagnostic assays advantageously display increased specificity, sensitivity and breadth of detection capability, compared to prior art assays. The assays are used in both human and veterinary settings in a wide range of assay formats including but not limited to enzyme linked immunofluorescence assays (ELISA), indirect fluorescent assays (IFA), immunoblot (also referred to as western blots), lateral flow and other immunoassay formats.

In other aspects, the invention also provides immunogenic and vaccine compositions comprising the chimeric OspC epitope protein and genetically engineered OspE *Borrelia* antigenic constructs described herein that can be used to prevent and or treat Lyme disease in humans and or animals.

It is an object of this invention to provide a polypeptide comprising i) SEQ ID NO: 2 (RM9A61) or a variant thereof having at least 90% amino acid sequence identity or similarity to SEQ ID NO: 2; or ii) SEQ ID NO: 4 (EurAs9v2) or a variant thereof having at least 90% amino acid sequence identity or similarity to SEQ ID NO: 4; or iii) a recombinant OspE mutant that does not bind factor H, with a caveat that if said recombinant OspE mutant that does not bind factor H is a BBL-39 polypeptide, then the polypeptide does not have an amino acid sequence that is identical to SEQ ID NOS: 11-26. In some aspects, the recombinant OspE mutant that does not bind factor H is SEQ ID NO: 29 (BBN38-13), SEQ ID NO: 31 (BBN38-37), SEQ ID NO: 28 (BBN38-20), SEQ ID NO: 30 (BBN38-25), SEQ ID NO: 32 (BBN38-7), SEQ ID NO: 33 (BBN38-5), SEQ ID NO: 34 (BBN38-31), SEQ ID NO 35 (BBN38-32), SEQ ID NO: 11 (BBL39-100), SEQ ID NO: 12 (BBL39-75), SEQ ID NO: 14 (BBL39-9), SEQ ID NO: 15 (BBL39-8), SEQ ID NO: 16 (BBL39-103), SEQ ID NO 17 (BBL39-70), SEQ ID NO: 20 (BBL39-72), SEQ ID NO: 21 (BBL39-69), SEQ ID NO: 22 (BBL39-7), SEQ ID NO: 24 (BBL39-37), SEQ ID NO: 25 (BBL39-90), SEQ ID NO: 26 (BBL39-51); or a variant thereof having at least 90% amino acid sequence identity or similarity.

The invention also provides methods of detecting *Borrelia* infection in a subject, the methods comprising i) detecting one or both of OspC antibodies and OspE antibodies in a biological sample from the subject; and, if one or both of said OspC antibodies and OspE antibodies are detected, then ii) concluding that the subject is infected with *Borrelia*. In some aspects, the method further comprises: if the subject is infected with *Borrelia*, determining whether the *Borrelia* infection is early, middle or late stage by quantitating relative amounts of the OspC antibodies and said OspE antibodies in the sample. In other aspects, the method further comprises: if a quantity of OspC antibodies is greater than a quantity of OspE antibodies, then concluding that the *Borrelia* infection is an early stage infection; and if a quantity of OspC antibodies is less than a quantity of OspE antibodies, then concluding that the *Borrelia* infection is a late stage infection. In yet further aspects a) the step of detecting OspC antibodies is performed by exposing the sample to an antigenic polypeptide comprising two or more OspC loop 5/helix 5 pairs from a plurality of OspC types, and, b) the step of detecting OspE antibodies is performed by exposing the sample to at least one recombinant OspE mutant that does not bind factor H. In additional aspects, the plurality of OspC types are associated with human *Borrelia* infection and are selected from the group consisting of: T, U, B, E, K, H, N, C, and M; is further aspects, the plurality of OspC types are associated with human *Borrelia* infection and are selected from the group consisting of: Pwa, Pli, PBes, Pki, PFim, Smar, HT22, A and K; and in yet further aspects, the plurality of OspC types are associated with canine *Borrelia* infection and are selected from the group consisting of types I, H, N, C, M, D, and F. In some aspects, the antigenic polypeptide further comprises an OspC type A protein. In additional aspects, the antigenic polypeptide further comprises an OspC type F protein. In further aspects, the antigenic polypeptide comprises a carboxy terminal sequence PVVAESPKKP (SEQ ID NO: 9). In yet further aspects, the at least one recombinant OspE mutant that does not bind factor H is one or both of BBN38-13 (SEQ ID NO: 29) and BBL39-9 (SEQ ID NO: 14). In additional aspects, the antigenic polypeptide comprising two or more OspC loop 5/helix 5 pairs from a plurality of OspC types is A12CF (SEQ ID NO: 1).

The invention further provides reconstituable powders comprising a polypeptide comprising i) SEQ ID NO: 2 (RM9A61) or a variant thereof having at least 90% amino acid sequence identity or similarity to SEQ ID NO: 2; or ii) SEQ ID NO: 4 (EurAs9v2) or a variant thereof having at least 90% amino acid sequence identity or similarity to SEQ ID NO: 4; or iii) a recombinant OspE mutant that does not bind factor H, with a caveat that if said recombinant OspE mutant that does not bind factor H is a BBL-39 polypeptide, then the polypeptide does not have an amino acid sequence that is identical to SEQ ID NOS: 11-26. In some aspects, the recombinant OspE mutant that does not bind factor H is SEQ ID NO: 29 (BBN38-13), SEQ ID NO: 31 (BBN38-37), SEQ ID NO: 28 (BBN38-20), SEQ ID NO: 30 (BBN38-25), SEQ ID NO: 32 (BBN38-7), SEQ ID NO: 33 (BBN38-5), SEQ ID NO: 34 (BBN38-31), SEQ ID NO 35 (BBN38-32), SEQ ID NO: 11 (BBL39-100), SEQ ID NO: 12 (BBL39-75), SEQ ID NO: 14 (BBL39-9), SEQ ID NO: 15 (BBL39-8), SEQ ID NO: 16 (BBL39-103), SEQ ID NO 17 (BBL39-70), SEQ ID NO: 20 (BBL39-72), SEQ ID NO: 21 (BBL39-69), SEQ ID NO: 22 (BBL39-7), SEQ ID NO: 24 (BBL39-37), SEQ ID NO: 25 (BBL39-90), SEQ ID NO: 26 (BBL39-51); or a variant thereof having at least 90% amino acid sequence identity or similarity.

The invention also provides compositions comprising a polypeptide comprising i) SEQ ID NO: 2 (RM9A61) or a variant thereof having at least 90% amino acid sequence identity or similarity to SEQ ID NO: 2; or ii) SEQ ID NO: 4 (EurAs9v2) or a variant thereof having at least 90% amino acid sequence identity or similarity to SEQ ID NO: 4; or iii) a recombinant OspE mutant that does not bind factor H, with a caveat that if said recombinant OspE mutant that does not bind factor H is a BBL-39 polypeptide, then the polypeptide does not have an amino acid sequence that is identical to SEQ ID NOS: 11-26; and a liquid vehicle. In some aspects, the recombinant OspE mutant that does not bind factor H is SEQ ID NO: 29 (BBN38-13), SEQ ID NO: 31 (BBN38-37), SEQ ID NO: 28 (BBN38-20), SEQ ID NO: 30 (BBN38-25), SEQ ID NO: 32 (BBN38-7), SEQ ID NO: 33 (BBN38-5), SEQ ID NO: 34 (BBN38-31), SEQ ID NO 35 (BBN38-32), SEQ ID NO: 11 (BBL39-100), SEQ ID NO: 12 (BBL39-75), SEQ ID NO: 14 (BBL39-9), SEQ ID NO: 15 (BBL39-8), SEQ ID NO: 16 (BBL39-103), SEQ ID NO 17 (BBL39-70), SEQ ID NO: 20 (BBL39-72), SEQ ID NO: 21 (BBL39-69), SEQ ID NO: 22 (BBL39-7), SEQ ID NO: 24 (BBL39-37), SEQ ID NO: 25 (BBL39-90), SEQ ID NO: 26 (BBL39-51); or a variant thereof having at least 90% amino acid sequence identity or similarity.

Also provided herein are devices for detecting *Borrelia* OspC antibodies and OspE antibodies in a biological sample, the devices comprising a substrate; and an antigenic polypeptide comprising two or more OspC loop 5/helix 5 pairs from a plurality of OspC types and at least one recombinant OspE mutant that does not bind factor H immobilized on the substrate. In some aspects, the substrate is a strip and the antigenic polypeptide and the at least one recombinant OspE mutant are immobilized at separate locations on the strip. In other aspects, the substrate is a multiwell plate and the antigenic polypeptide and the at least one recombinant OspE mutant are immobilized in separate wells of the multiwell plate.

The invention also provides vaccines and/or immunogenic compositions comprising: one or more antigenic polypeptides selected from the group consisting of: SEQ ID NO:

2 (RM9A61) or a variant thereof having at least 90% amino acid sequence identity or similarity to SEQ ID NO: 2; SEQ ID NO: 4 (EurAs9v2) or a variant thereof having at least 90% amino acid sequence identity or similarity to SEQ ID NO: 4; and a recombinant mutant OspE protein that does not bind factor H; and a physiologically compatible carrier. In some aspects, the recombinant mutant OspE protein that does not bind factor H is selected from the group consisting of SEQ ID NO: 29 (BBN38-13), SEQ ID NO: 31 (BBN38-37), SEQ ID NO: 28 (BBN38-20), SEQ ID NO: 30 (BBN38-25), SEQ ID NO: 32 (BBN38-7), SEQ ID NO: 33 (BBN38-5), SEQ ID NO: 34 (BBN38-31), SEQ ID NO 35 (BBN38-32), SEQ ID NO: 11 (BBL39-100), SEQ ID NO: 12 (BBL39-75), SEQ ID NO: 14 (BBL39-9), SEQ ID NO: 15 (BBL39-8), SEQ ID NO: 16 (BBL39-103), SEQ ID NO 17 (BBL39-70), SEQ ID NO: 20 (BBL39-72), SEQ ID NO: 21 (BBL39-69), SEQ ID NO: 22 (BBL39-7), SEQ ID NO: 24 (BBL39-37), SEQ ID NO: 25 (BBL39-90), SEQ ID NO: 26 (BBL39-51); or a variant thereof having at least 90% amino acid sequence identity or similarity.

Also provided are methods of preventing or treating Lyme disease in a subject (e.g. a subject in need thereof), comprising administering to the subject a therapeutically effective dose of a composition comprising one or more antigenic polypeptides selected from the group consisting of: SEQ ID NO: 2 (RM9A61) or a variant thereof having at least 90% amino acid sequence identity or similarity to SEQ ID NO: 2; SEQ ID NO: 4 (EurAs9v2) or a variant thereof having at least 90% amino acid sequence identity or similarity to SEQ ID NO: 4; and a recombinant mutant OspE protein that does not bind factor H; and a physiologically compatible carrier.

Also provided are methods of preventing or treating Lyme disease in a subject (e.g. a subject in need thereof), comprising administering to the subject a therapeutically effective dose of a composition of recombinant mutant OspE protein that does not bind factor H is selected from the group consisting of SEQ ID NO: 29 (BBN38-13), SEQ ID NO: 31 (BBN38-37), SEQ ID NO: 28 (BBN38-20), SEQ ID NO: 30 (BBN38-25), SEQ ID NO: 32 (BBN38-7), SEQ ID NO: 33 (BBN38-5), SEQ ID NO: 34 (BBN38-31), SEQ ID NO 35 (BBN38-32), SEQ ID NO: 11 (BBL39-100), SEQ ID NO: 12 (BBL39-75), SEQ ID NO: 14 (BBL39-9), SEQ ID NO: 15 (BBL39-8), SEQ ID NO: 16 (BBL39-103), SEQ ID NO 17 (BBL39-70), SEQ ID NO: 20 (BBL39-72), SEQ ID NO: 21 (BBL39-69), SEQ ID NO: 22 (BBL39-7), SEQ ID NO: 24 (BBL39-37), SEQ ID NO: 25 (BBL39-90), SEQ ID NO: 26 (BBL39-51); or a variant thereof having at least 90% amino acid sequence identity or similarity.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

FIG. 1. Organization and sequence of A12CF (SEQ ID NO: 1), an exemplary chimeric construct. L5 indicates a loop 5 epitope and H5 indicates a helix 5 epitope. The designation following L5 or H5 indicates the OspC type from which the epitopes sequences are derived (the term "type" is used to differentiate distinct variants of the OspC protein that have been identified through phylogenetic analyses). A full length type F OspC is included at the C-terminus of the A12CF "chimeritope". "Chimeritope" refers to novel amino acid sequences (recombinant proteins) that possess a chimeric epitope-based domain comprised of two or more linear epitopes from one or more proteins (or protein variants) derived from one or more pathogenic species of microbes. Chimeritopes detailed here include specific linear epitopes from multiple OspC variants that are derived from several species of *Borrelia* that cause Lyme disease in humans and other mammals. The chimeritopes may or may not include a full length OspC protein at the carboxy terminal end of the construct. It should be noted that the leader peptide of the "full length" or extended segments of the OspC proteins included in some chimeritopes do not include a leader peptide. A12CF harbors a "full length" type F OspC protein that is fused to the C-terminal end of the chimeric domain.

FIG. 2. Organization and sequence of RM9A61 (SEQ ID NO: 2), an exemplary chimeric construct. L5 indicates a loop 5 epitope and H5 indicates a helix 5 epitope. The designation following L5 or H5 indicates the OspC type the sequence is derived from. A "full length" type A OspC (minus the leader peptide) with a specifically engineered amino acid substitution (E61 to Q61) is included at the C-terminus of this chimeritope. This construct was specifically designed to detect antibodies that develop against variants of the Lyme disease spirochetes that are most commonly associated with human and veterinary infections in North America.

FIG. 3. Organization and sequence of A9v2 (SEQ ID NO: 3), an exemplary chimeric construct. L5 indicates a loop 5 epitope and H5 indicates a helix 5 epitope. The designation following L5 or H5 indicates the OspC type the linear epitope sequence is originally derived from. In contrast to A12CF and RM9A61 described above, the A9v2 construct does not have a full length OspC at its C-terminus. Instead, the C10 domain of OspC is included at the C-terminus of the protein.

FIG. 4. Organization and sequence of EurAs9v2 (SEQ ID NO: 4), an exemplary chimeric construct. L5 indicates a loop 5 epitope whereas H5 indicates a helix 5 epitope. The designation following L5 or H5 indicates the OspC type the sequence is derived from. The C10 domain of OspC is included at the C-terminus of the protein. This construct was specifically designed to detect antibodies that develop against variants of the Lyme disease spirochetes that are most commonly associated with human, wildlife and veterinary infections in Europe.

FIG. 8. Identification of amino acid residues in the OspE protein, BBL39, that influence binding of host derived ligands and antibody. The OspE proteins have been demonstrated to bind an abundant mammalian serum protein referred to as factor H (FH). OspE proteins, which are produced during late stage infections, elicit antibody responses that are indicative of a late stage infection. To generate BBL39 modified variants that do not bind FH, and which would therefore have better ability to bind Ab that develops to the BBL39 protein, the BBL39 gene derived from *B. burgdorferi* strain B31 was cloned and subjected to random mutagenesis. The sequence indicated as "L39wt" is the native sequence (i.e., wild type). After conducting random mutagenesis of a cloned copy of L39wt, the resulting mutants that were obtained were tested for FH binding and ability to bind antibody that is produced against BBL39 during infection in mice (binding results are indicated as + or − and the number of amino acids residues that were altered in each mutants is indicated (#m). The designations on the left indicate the *Escherichia coli* clone that carried the mutated gene and produced the mutated protein. Note that the designations assigned to each clone are arbitrary designations that were assigned in order to track each clone. The asterisk at the end of each sequence indicates a stop codon (i.e., a sequence that causes termination of protein translation). Periods listed for other sequences indicate residues that are identical to the corresponding L39wt sequence (amino acid). Note that the sequences do not include the leader peptide. The DNA sequence encoding the leader peptide was omitted from the final construct because leader peptides are commonly known to inhibit high level of recombinant protein production in *E. coli*. The aligned sequences (using a designation that omits "BB") are as follows: L39wt ("wild type", SEQ ID NO: 10), L39-100 (SEQ ID NO: 11), L39-75 (SEQ ID NO: 12), L3984 (SEQ ID NO: 13), L39-9 (SEQ ID NO: 14), L39-8 (SEQ ID NO: 15), L39-103 (SEQ ID NO: 16), L39-70 (SEQ ID NO: 17), L39-67 (SEQ ID NO: 18), L39-88 (SEQ ID NO: 19), L39-72 (SEQ ID NO: 20), L39-69 (SEQ ID NO: 21), L-39-7 (SEQ ID NO: 22), L-39-48 (SEQ ID NO: 23), L39-37 (SEQ ID NO: 24), L39-90 (SEQ ID NO: 25), and L39-51 (SEQ ID NO: 26).

FIG. 9. Identification of amino acid residues in the OspE protein, BBN38, that influence binding of host derived ligands and antibody. As described in FIG. 8, the OspE proteins have been demonstrated to bind an abundant mammalian serum protein referred to as factor H (FH) and to elicit antibody responses that are indicative of a late stage infection. To generate BBN38 modified variants that do not bind FH, and which would therefore have better ability to bind Ab, the BBN38 gene derived from *B. burgdorferi* strain B31, was cloned and subjected to random mutagenesis. The sequence listed as "N38wt" is the native sequence (i.e., wild type). After conducting random mutagenesis of a cloned copy of N38wt, the resulting mutants that were obtained were tested for FH binding and ability to bind antibody that is produced against BBN38 during infection in mice (binding results are indicated as + or − and the number of amino acids residues that were altered in each mutants is indicated (#m). The designations on the left indicate the *Escherichia coli* clone that carried the mutated gene and produced the mutated protein. The asterisk at the end of each sequence indicates a stop codon. Periods listed for other sequences indicate residues that are identical to the L39wt amino acid sequence. As detailed in FIG. 8, the leader peptide sequence was not included in the construct because it's inclusion inhibits production of recombinant proteins in *E. coli*. The aligned sequences (using a designation that omits "BB") are as follows: N38wt: (SEQ ID NO: 27), N38-20 (SEQ ID NO: 28), N38-13 (SEQ ID NO: 29), N38-25 (SEQ ID NO: 30), N38-37 (SEQ ID NO: 31), N38-7 (SEQ ID NO: 32), N38-5 (SEQ ID NO: 33), N38-31 (SEQ ID NO: 34) and N38-32 (SEQ ID NO: 35).

FIG. 12. The amino acid sequence of native (wild type) type A OspC protein. The sequence of the *B. burgdorferi* OspC protein (type A) from strain B31 is shown and amino acid positions are numbered. The location of regions of the protein that are relevant to this application are indicated.

FIG. 13A-D. Amino acid sequences of antigenic constructs. A, A10CF (SEQ ID NO: 5); B, A11 (SEQ ID NO: 6); C, A12 (SEQ ID NO: 7); D, A12A (SEQ ID NO: 8).

FIG. 14. Geographical distribution of representative OspC types.

FIG. 15. Determination of the level of non-specific Ab in healthy canines. To determine the appropriate ELISA value for reaching a positive or negative diagnosis of Lyme disease, serum was collected from 78 purpose bred beagles and the level of non-specific antibody determined by ELISA using A12CFR, BBN38 and BBL39-9. All dogs were previously confirmed to be seronegative for Lyme disease using the commercially available SNAP-4Dx test and an independent in house immunoblot assay that used immobilized *B. burgdorferi* strain B31 cell lysate as the membrane immobilized detection antigen. Serum from clinically confirmed and serologically positive dog (Can Pos) served as the positive control. To conduct the ELISA's, the A12CF, BBN38 and BBL39-9 proteins were immobilized in triplicate in the wells of an ELISA plate. The plates were then screened with a 1:100 dilution of each serum sample and the absorbance values at 405 nm determined. The data are presented as the average ELISA units for the three wells with standard deviations indicated. The final column presents the sum of the ELISA units obtained with all antigens. The average value for non-specific or background ELISA units for the 78 dogs tested was determined to be 1895 (ELISA units). Based on ELISA results obtained with additional LD positive canine serum samples it was determined that a positive diagnosis can be made when the level of antibody is 1.2 fold greater than the background levels in healthy dogs.

FIG. 16. Demonstration of the ability of A12CF and OspE antigens to diagnose Lyme disease in canine patients. Canine serum samples were purchased from a commercial diagnostic laboratory and were originally obtained by that facility from canine patients that presented at veterinary clinics. The Can Pool neg and Can Pos serum samples are positive and negative controls respectively. The negative control serum is a pooled serum sample. The data presented in tabulated form in the figure are the results of ELISA analyses using the A12CF, BBN38 and BBL39-9 as the antibody detecting proteins. Absorbance values were obtained and the data converted to ELISA units. A positive diagnosis was concluded if the sum of ELISA units for the three antigens was 1.2 fold over that value obtained for the well characterized pool of negative control canine serum samples (i.e., a positive diagnosis was concluded from a total EU values equal to or greater than 1800). The results obtained with A12CF, BBN38 and BBL39-9 recombinant proteins were compared with results obtained by the commercial laboratory using the SNAP4Dx test (score as positive, negative, or weakly positive) or by in house immunoblot analysis (scored as positive, negative or weak) using membrane immobilized *B. burgdorferi* B31. A weak immunoblot result is typified by low intensity detection of proteins in the 37 kDa range (consistent with the flagellin protein).

DETAILED DESCRIPTION

Figure 5A:
FIGS. 5A and B. Ligand binding domain 1 (LBD1) of OspC. A, atomic structure of a natural (native) OspC dimer. LBD1 is boxed and expanded in B. The position of E61 and other residues that influence OspC function are shown.
Figure 5B:
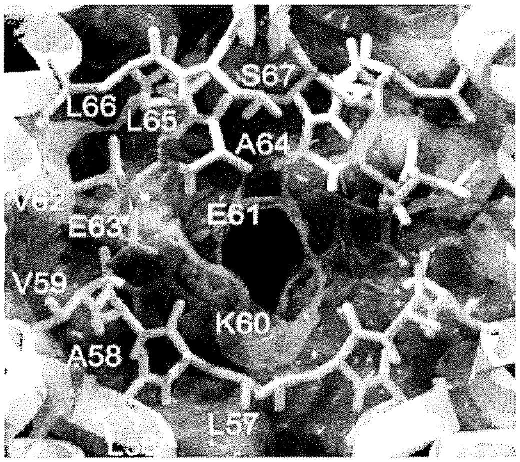

The profile of antibodies that develop in a mammal infected with *Borrelia burgdorferi* changes over the course of infection. For example, production of the lipoprotein OspC, which is not produced in unfed ticks, is significantly upregulated after the ticks initiate a mammalian blood meal and continues at a high level for several weeks to a few months after the spirochetes enter the mammalian host. During that time OspC elicits a very strong Ab response which is indicative of early stage infection. After several weeks to a few months, the production of OspC is down regulated (i.e., less is made or production is turned off completely) and the concentration of circulating anti-OspC-antibodies present in the blood and other bodily fluids decreases. During later stages of the disease, proteins belonging to the OspE protein family (BBL39 and BBN38) are upregulated. OspE plays an important role in the pathogenesis of Lyme disease spirochetes by facilitating immune evasion. Specifically, OspE proteins bind a mammalian derived protein called factor H (FH) sequestering it at the bacterial cell surface. FH is produced by all mammals and is a negative regulator of the complement system, an important arm of innate immunity. The binding of FH to the *Borrelia* surface facilitates complement evasion by the bacteria by locally downregulating the destructive effects of complement at the cell surface, thereby helping to maintain the *Borrelia* infection.

Accordingly, two distinct classes of diagnostic antigens, one of which is specific for detecting OspC (or isolated epitopes derived from OspC) and the other of which is specific for detecting OspE proteins, have been developed. The antigens are either chimeric, genetically engineered proteins ("chimeritopes") or recombinant mutant proteins, with properties that are distinct from the naturally occurring proteins (as produced by Lyme disease spirochetes) from which they are derived. The proteins are unique in that their engineered molecular design allows them to be used not only to diagnose active Lyme disease in a "yes or no" fashion (as current tests seek to do) but, significantly, to also differentiate among early, mid- and late stage *Borrelia* infections when used side by side in a multiprotein assay.

In addition, the OspC chimeritope proteins are advantageous for use in diagnostics and vaccines because regions of the native protein that are problematic in terms of structural maintenance, unfavorable folding, eliciting adverse events, blocking important epitopes, and/or eliciting non-productive immune responses (i.e., non-bactericidal or non-protective Ab) have been purposefully eliminated.

Multiprotein diagnostic assays using the antigens are described herein. In some aspects, the assays are serologically based assays which measure the presence and/or concentration of antibodies to the early stage OspC and late stage OspE proteins to detect *Borrelia* infection. If the results of an assay indicate that a subject is infected (e.g. if anti-*Borrelia* antibodies are detected), the relative amounts of early (anti-OspC) and late (anti-OspE) stage antibodies are used to classify the stages of infection. The Examples provided herein demonstrate that assays using the chimeric antigens effectively diagnose Lyme disease in canines and humans with high sensitivity and specificity, and accurately distinguish between early, mid- and late stage infection. In fact, the results show that the antigens of the invention provide superior diagnostic accuracy, when compared to tests which are currently employed for Lyme disease diagnosis.

Vaccine and immunogenic compositions comprising certain of the antigens are also provided, as are methods of using the compositions.

The following terms and definitions are used throughout:

The phrase "early stage infection" refers to a period of time during which OspC is produced by *Borrelia* bacteria while inside an infected mammal. "Late stage" refers to the period of time during infection after production of OspC has ceased. Parameters for quantitating these stages, as well as mid-stage infection, are described herein. The exact timeframe during which OspC is produced can vary depending on the infecting strain, the host species, attributes of the individual infected mammal, and other factors, hence a precise timeframe cannot be assigned to each stage. The use of the methods described herein for assigning a stage of infection to a subject obviates the need to rely on such factors.

"Chimeritope" refers to amino acid sequences that possess a chimeric epitope-based domain comprised of two or more linear epitopes from one or more proteins (or protein variants) derived from one or more pathogenic species of microbes. Herein, these constructs may also be referred to as chimeras, fusion proteins, polypeptides, antigenic constructs, and/or by other similar words and phrases. The chimeritopes described herein are generally based on OspC sequences that are representative of the numerous species or types of Lyme disease spirochetes that cause human and veterinary Lyme disease.

A "chimeric domain" refers to the segment (portion, etc.) of a chimeritope that comprises a plurality of linear epitopes. In the context of the OspC epitope based chimeritopes described here the specific epitopes that are included in the constructs are the loop 5 (L5) and alpha helix 5 (H5) epitopes. Several L5 and H5 epitopes derived from diverse Lyme disease spirochete isolates are included in the chimeritope. Note that the terms "loop5" and "helix 5" epitopes are not intended to imply that the sequence of the L5 and H5 epitopes consists solely of amino acids residues contained within a the loop5 or helix 5 structural elements of OspC. Instead these terms indicate the general region of OspC in which these epitopes reside. An L5 epitope for example may include a small number of flanking amino acid residues that are not structurally contained with loop 5 epitope per se. In the chimeritopes, multiple L5/H5 epitope pairs from different OspC types are joined. The chimeric domain is also referred to herein as the "first segment" of an early stage chimera. In some embodiments of the chimeritopes the chimeric domain is fused to the N-terminus of a full length OspC protein (with the exception that the full length protein lacks its leader peptide). This "full length" portion of the construct may be referred to as the "second segment" of the construct. It is important to note that the precise atomic structures of several OspC proteins have been determined. Hence the loop5 (L5) and helix5 (H5) designations used here are not arbitrary and the use of these terms is based on the well characterized structural elements of OspC.

"Full-length" is intended to encompass actual full-length versions of an Osp protein, or, alternatively, one or more relatively large segments of the full-length sequence, e.g. at least about 50, 55, 60, 65, 70, 75, 80, 85, 90 or 95% (or more) of the full-length sequence. The included segment(s) comprise(s) a linear sequence of amino acids joined contiguously in the same order (in the amino to carboxy terminal direction) as occurs in the native protein, although the segments may be separated by internal deletions, and deletions may occur at either the native carboxy or amino terminus. Further, as described elsewhere herein, the chimeritope may include various amino acid linker sequences that serve to connect individual L5 and H5 epitopes, L5/H5 epitope pairs or the chimeric domain to the "full length" ospC domain. A full length segment is generally located at the carboxy terminus of the chimeric domain of a chimeritope but may be present at the amino terminus or in the midst of a chimeric domain instead, and may be directly joined thereto or separated by a linking (linker, spacer, etc.) sequence.

A "linker sequence" (also linking or spacer sequence) refers to a relatively short linear amino acid sequence (e.g. from about 1 to about 10 amino acids) that is usually not derived from an Osp protein and which does not generally contribute to eliciting an immune response or detecting antibodies, but rather serves to join two sequences of interest together. Linker sequences may be purposefully introduced in order to separate sequences or may be present, for example, due to adventitious nucleic acid encoding sequences in a vector from which a sequence is translated.

"Naturally occurring antibodies" are those which are made by a subject due to exposure or infection of the subject by a *Borrelia* spirochete (e.g. due to a tick bite, either in the wild, or experimentally or accidentally induced), or, alternatively, due to the subject having been vaccinated with a Lyme disease vaccine. In some aspects, it may be useful to detect previous vaccination, or the efficacy of previous vaccination, of a subject.

"Substantially pure" refers to a composition in which a macromolecular species (e.g. a polypeptide) is the predominant species present. On a molar or weight basis, it is more abundant than any other individual macromolecular species in the composition e.g. at least about 50, 60, 70, 80, 90, 95, 96, 97, 98, or 99% or more percent of the macromolecular species present by mole or % weight. The object species may be purified to essential homogeneity (i.e., contaminant species cannot be detected in the composition by conventional detection methods). Solvent species, small molecules (<500 Daltons), and elemental ion species are not considered macromolecular species.

OspC Chimeritopes: Early Stage Diagnostic Antigens

As discussed above, the "early diagnostic antigens" described herein are recombinant chimeric proteins comprised of a series of specifically selected linear epitopes that have been identified in OspC. The linear epitopes included in the OspC chimeras are referred to as the Loop 5 (L5) and Helix 5 (H5) epitopes. The L5 and H5 epitopes were identified by screening extensive panels of differently sized fragments of OspC with serum from infected humans and animals using immunoblot based analyses or by screening panels of overlapping OspC derived peptides. The screening experiments identified these two well-defined segments of the protein as immunoreactive with the majority of serum samples tested.

The OspC based chimeritopes are thus polypeptides that are comprised of two or more L5/H5 epitope pairs from different isolates or species of the bacteria that cause Lyme disease. As such, in the context of a diagnostic antigen, the chimeritopes detect Ab that develops against diverse OspC proteins produced by different Lyme disease spirochete strains or species during natural infection, and, in the context of vaccines, they elicit antibodies that bind to diverse OspC proteins from different strains.

Loop 5 (L5) of native OspC is defined in the art as including residues 131 to 149 and helix 5 (H5) is defined as including residues 160 to 200 of the native OspC protein. It is important to note that some OspC variants have natural short insertions or deletions that precede or occur within the L5 and H5 epitopes so the numbering cited in the previous sentence can vary slightly; thus, the numbers listed above are not used to define the absolute boundaries of the L5 and H5 epitopes. The reference wild type OspC sequence on which the numbering used herein is based (from *B. burgdorferi* strain B31) is depicted in FIG. 12. In this figure, the L5 and H5 epitope sequences are highlighted. As can be seen, in naturally occurring, native OspC, the L5 and H5 epitopes are separated by an intervening sequence that contains portions of alpha helix 4 and loop 6. Through rigorous analyses of the immune responses to proteins that have these intervening sequences, the present inventors found that these intervening segments are generally not beneficial in diagnostic and vaccine constructs. Hence, in the present antigens, most of the intervening sequence has been removed, thereby generating a synthetic fusion of the L5 and H5 epitopes to form a conjoined L5/H5 epitope pair that lacks alpha helix 4 and loop 6. In other words, alpha helix 4 and loop 6 are absent from the conjoined L5/H5 epitope pair. Among other advantages, the removal of helix 4 and loop 6 advantageously allows for the generation of chimeric proteins that accommodate a larger number of L5/H5 epitope pairs than would be practically possible if the intervening sequences were maintained. For the same reason, segments of some of the included L5 and H5 epitopes that are present in more than one L5 and H5 epitope in the polypeptides have also been removed.

Thus, as used herein, the phrases "L5 and H5 epitope pair" and "L5/H5 epitope pair" refer to a synthetic polypeptide or amino acid sequence in which an L5 epitope and an H5 epitope are fused together, either directly or, optionally, with a short intervening synthetic linking sequence that is not native to the OspC protein, or optionally, with a short intervening sequence that includes a few (e.g. from about 1 to about 10 or more) flanking amino acids that are adjacent to the L5 and/or H5 epitopes in the native protein. Therefore, as used herein, the terms "L5" and "H5" (or phrases such as "L5 epitope", "H5 epitope", "L5 region", "H5 region", "L5 sequence" and "H5 sequence", etc.) refer to contiguous linear amino acid sequences which, when present in a chimeric protein, may optionally include a portion of naturally occurring flanking sequence at one or both of the carboxy and amino termini of one or both of the epitopes per se. In other words, L5 and H5 do not necessarily consist of precisely numbered residues of the native OspC protein, but typically do comprise those sequences. For example, in the chimeric constructs, from about 1 to about 10 or more flanking amino acids may be retained at one or both of the carboxy and amino terminal ends of one or both of L5 and H5 epitopes.

It has largely been held that sequence variation among OspC proteins from different *Borrelia* species is too great to allow for its use in a vaccine or diagnostic assay. However, phylogenetic analyses by the present inventors of several hundred OspC sequences, and specifically the L5 and H5 regions, showed that the variation is not insurmountable, and that all OspC sequences fall into one of ~30 distinct major variants or phyletic types. Further, only a subset of OspC types is associated with strains that infect canines or humans with significant frequency, and the L5/H5 epitope variants that are most frequently recovered from infected canines versus infected humans differ. Based on this, an OspC based chimeric antigen need not contain all known L5/H5 epitope pairs from all ~30 OspC types. Rather, L5/H5 chimeric proteins are tailored to the target species and or geographic area to include the most relevant L5/H5 epitope pairs for the target population (e.g. human, canine, wildlife, horses, etc). Further, a chimera that harbors a sufficient number of appropriately selected diverse epitope pairs can detect Ab that was generated during infection to other closely related L5 and or H5 epitopes, even though sequences identical to the closely related L5 and or H5 epitopes themselves are not included in the chimera, affording broad detection and/or protection against the numerous diverse species that comprise the *B. burgdorferi* sensu lato complex. Generally, at least 4 L5/H5 epitope pairs are present in an antigenic polypeptide. Typically each L5/H5 pair is derived from a different OspC type, although this is not always the case as in some instances repeating a given L5/H5 epitope pair can be beneficial for enhancing the detection sensitivity of that sequence or enhance immune responses elicited to a given epitope pair Preferred OspC types for use in early stage diagnostic antigens for canines and companion animals in North American include, for example, OspC types A, B, C, D, E, F, H, I, K, M, and N. These OspC types were selected based on experiments which demonstrated that they are most commonly associated with Lyme disease strains that infect canines and companion animals in North American. However, L5/H5 pairs from other OspC types may also be included or substituted for the types preferred for canines and companion animals. An exemplary OspC-based chimeritope harboring several of these types, A12CF (SEQ ID NO: 1), is shown in FIG. 1. A12CF comprises an N-terminal or first segment of L5/H5 epitopes pairs derived from OspC types I, H, N, C, M and D. In addition, A12CF includes a carboxy or second segment of full-length OspC type F spanning residues 20 to 210, which lacks the natural leader peptide and is fused to the L5/H5 chimeric domain. Due to the repeated nature of the L5/H5 epitope pairs, a beneficial cross reactivity with the epitope pairs is observed with Ab elicited by a different pair. For this reason it is not required that every OspC type be represented in the construct. In addition, in a canine-tailored chimera as in A12CF, when a full-length OspC protein is included, a type F is preferred. However, it is possible to substitute a different type and still obtain good results in canines and other animals. We have demonstrated this using the RM9A61 construct (described below) which possesses a different set of L5/H5 epitope pairs fused to a full length type A OspC. All such variants are encompassed by the present invention.

As indicated above, an OspC chimeritope that is intended for use as a human vaccine or diagnostic antigen generally possesses a set of L5/H5 epitopes, and, optionally, a full length OspC protein, that may differ from some of those selected for canines. For example, for human applications, type A, B, C, E, H, I, K, N, M, T and U epitopes and proteins are preferred, as these OspC types are more commonly associated with human infection. However, L5/H5 pairs from other OspC types may also be included or substituted for the types preferred for humans. In addition, for human-focused constructs, position E61 (position numbering based on the native protein; see native protein sequence, SEQ ID NO: 5, in FIG. 12) is generally changed to a Q or other suitable residue. The presence of a Q at position 61 is not a naturally occurring variant. While the precise function of OspC in mammals is unknown, it is known that introduction of an amino acid substitution at position E61 eliminates the ability of the Lyme disease spirochete to infect mammals. In the native protein, residue E61 is thought to be involved in the binding of the mammalian derived ligand. Without being bound by theory, it appears that disruption of this putative ligand binding site renders the chimeric proteins more accessible for binding Ab that develops during natural infection, e.g. in diagnostic applications, and for eliciting Ab production in vaccine applications.

E61 can be substituted by any amino acid residue that has the effect of rendering the Lyme disease spirochetes non-infectious. Further, mutations of other OspC residues may also render the spirochetes non-infectious and all such mutants are encompassed herein. For example, the mutation of position K70 allows the spirochetes to infect a host but attenuates their ability to disseminate, so that they are also non-infectious. The rationale for using a site-directed mutant of OspC as part of the constructs described herein is two-fold. First, for a diagnostic, preventing host derived ligand in biological samples from binding to OspC eliminates or decreases steric hindrance to antibody binding sites, augmenting the amount of bound antibody and thus the amount of detectable signal (if antibodies are in fact present). Second, for a vaccine, preventing the binding of host-derived ligand to the protein increases accessibility of host antibodies to the protein during an immune response to infection.

An exemplary embodiment of a human-oriented construct for use in North America, RM9A61 (SEQ ID NO: 2), is depicted in FIG. 2. RM9A61 comprises L5/H5 epitope pairs derived from OspC types T, U, B, E, K, H, N, C, and M. This chimeric domain is fused to a segment of type A OspC (the full length protein lacking the leader domain). Other exemplary OspC chimeritopes that can be used as diagnostic antigens for early detection of infection or as vaccine for use in North American include but are not limited to A9v2 (FIG. 3, SEQ ID NO:3), A10CF (FIG. 13A, SEQ ID NO: 5), A11 (FIG. 13B, SEQ ID NO:6), A12 (FIG. 13C, SEQ ID NO: 7) and A12A (FIG. 13D, SEQ ID NO: 8), and variants of the same as disclosed herein.

In addition, in some aspects, the OspC chimeritopes have been designed to include L5/H5 epitope pairs from other selected geographic regions. For example, the preferred OspC chimeritopes for diagnosing early stage infection in Europe and Asia and or vaccination are highlighted in FIG. 4 (SEQ ID NO:4) in the EurAs9v2 construct. The OspC types in this construct include but are not necessarily limited to Pwa, Pli, PBes, Pki, PFim, Smar, HT22, A, and K. Such geographically focused proteins may be used in separate diagnostic assays or vaccines designed for a particular region of interest (e.g. North America, Europe, etc.) or they may be included in a single assay or vaccine formulation that is appropriate for use in multiple regions. Alternatively, a plurality of different regionally-focused L5/H5 epitope pairs may be present in a single chimeric polypeptide and efficiently used as a diagnostic or in a vaccine in multiple locations.

EurAs9v2 and A9v2 differ from RM9A61 and A12CF, respectively, in that they include only L5/H5 epitope pairs; a full length OspC protein is not included in these constructs. In other words, they do not include a native or modified extended segment of OspC following the chimeric domain. However, in these exemplary constructs, the chimeric domains are fused to 10 residues typically found at the C-terminus of OspC proteins, the "C10 domain", PVVAESPKKP (SEQ ID NO: 9). This 10 aa sequence is highly conserved in OspC and is included in the chimeritope to protect the C-terminus of constructs from proteolytic degradation. The L5/H5 epitope pairs in EurAs9v2 include epitopes derived from OspC sequences obtained from strains that were collected or detected in Europe, together with L5/H5 pairs from two North American OspC types (A and K). The L5/H5 epitope pairs in A9v2 are derived from OspC types A, B, K, I, H, N C, M, and D. A9v2 has proven highly effective as a vaccine antigen in canines and is also well suited for use as a diagnostic antigen.

Data presented in FIG. 14 may be used, for example, to develop other suitable regionally focused constructs or construct segments, by selecting OspC types that are present in a region of interest.

OspE Antigenic Proteins: Late Stage Diagnostic Antigens

Diagnostic antigens that are specific for late stage infection are also encompassed by the present invention. The late stage diagnostic antigens are laboratory generated, genetically engineered, recombinant derivatives of naturally occurring OspE. Most Lyme disease spirochetes carry two or three different OspE related genes encoding the "OspE protein family". The different members of this family that are produced by a given strain are referred to as "OspE paralogs" while those produced by different strains are referred to as "OspE orthologs". The amino acid identity values of OspE orthologs range from 59 to 100%.

The Lyme disease spirochete ospE genes are found on circular plasmids of approximately 32 kb in size that are referred to as the "cp32 plasmids". All Lyme disease spirochete species that cause infections in mammals possess several distinct cp32 plasmids. For example, the *B. burgdorferi* type strain B31 carries 9 different cp32 plasmids, 3 of which carry genes that encode proteins belonging to the OspE gene/protein family. The three OspE paralogs produced by type strain B31 are designated as BBN38, BBL39 and BBP39. BBL39 and BBP39 are identical in sequence while BBN38 is distinctly different. Since BBL39 and BBN38 are identical in sequence and hence there is no need to differentiate them, we refer to these two proteins collectively as BBL39 throughout this document.

OspE proteins play an important role in the pathogenesis of Lyme disease spirochetes by facilitating immune evasion. Specifically, they bind the mammalian derived protein "factor H" (FH) to the bacterial cell surface. FH is produced by all mammals and it is a negative regulator of the complement system, an important arm of innate immunity. The binding of FH to the *Borrelia* surface facilitates complement evasion by the spirochete by locally downregulating the destructive effects of complement at the cell surface. FH is a highly abundant protein in the blood of mammals, with concentrations being as high as 450 ug/ml. As a result, when Lyme disease spirochetes infect a mammal, the OspE proteins presented on their surface quickly bind and become saturated with FH.

The present inventors used amino acid mutagenesis studies to identify OspE residues that, when altered, abolish FH binding but still allow for binding of antibody that develops against the OspE proteins during natural infection. In the context of a diagnostic antigen, the elimination of FH binding by OspE proteins is important because it prevents FH in serum or other samples from binding to the diagnostic antigens and sterically blocking Ab binding, which would otherwise decrease sensitivity of the diagnostic assay. OspE mutants that may be used in the practice of the invention include but are not limited to the exemplary sequences shown in FIGS. 8 and 9, namely BBL39-100, BBL39-75, BBL39-9, BBL39-8, BBL39-103, BBL39-70, BBL39-72, BBL39-69, BBL39-7, BBL39-37, BBL39-90, BBL39-51, BBN38-13, and BBN38-37. Additional modified variants that can be used would include but are not limited to: variants with mutations at the same residues (at the same positions) as those depicted but in which a different amino acid (different than an amino acid depicted in FIGS. 8 and 9) is substituted for the wild type residue(s) at one or more of the substituted positions; mutants comprising combinations of the substitutions depicted, e.g. with the same residues substituted but in a single polypeptide, such as a polypeptide in which S is replaced by L at position 82 (as in BBL39-9) and T is also replaced by P at position 9 (as in BBL39-72; and other mutants which possess the binding properties of the sequences (i.e. do not bind Factor H but do bind to antibodies that are made in response to a natural *Borrelia* infection). In the practice of the invention, any modified OspE based mutant may be used, as long as the mutant has the designed features that it binds to anti-OspE antibodies elicited during natural infection but lacks the ability to bind to FH.

Further, OspE antigenic constructs need not be limited to recombinant mutants but can also be chimeric or fusion proteins. As an example, to further increase the effectiveness of BBL39 for diagnostic and vaccine applications, a chimeric construct designated as L39-61/82 is used. L39-61/82 is comprised of residues 16 through 67 of BBL39-9 and residues 68 through 173 of BBL39-8. The 61/82 designation in L39-61/82 indicates the location of engineered amino acid substitutions that will allow for enhanced detection of antibody and elimination of FH binding. Position 61 and 82 can be any amino acid except proline, since a proline will disturb protein folding. Other chimeric OspE constructs comprising portions of other active OspE mutants may also be designed, and all which have the desired properties described herein are encompassed by the present invention.

In an assay, the use of both BBN38 and BBL39 protein variants is generally preferred, because some natural isolates carry one gene but not the other. Hence, designed variants of both BBL39 and BBN38 that have the properties described above, are usually components of the assay in order to ensure detection of anti-OspE targeting Ab. Experimental results presented in the Examples section below showed that mutated versions of OspE that did not bind FH were more sensitive when used to detect antibodies to OspE than was wild type OspE that does bind FH. Also, the results showed that OspE antibodies are not detected until late in a Lyme disease infection, confirming that antigens based on OspE are highly suitable for use in the multistage diagnostic assays of the invention.

Exemplary Sequences of the Chimeritopes, Antigenic Recombinant Mutants, and Variants Thereof Exemplary constructs that may be used in the practice of the diagnostic aspect of the present invention include but are not limited to: A12CF, RM9A61, A9v2, EurAs9v2, A10CF, A11, A12, A12A, BBL39-9, BBL39-8, BBL39-69, BBL39-70, BBL39-37, BBN38-13, and BBN38-37.

The exact composition of the constructs explicitly described herein may vary somewhat as long as the resulting variant retains that ability to bind to *Borrelia* antibodies in an assay and/or to elicit a suitable immune response when administered. Those of skill in the art will recognize that various other modified forms (variants or derivatives) of the amino acid sequences disclosed herein may be made, and the invention encompasses all such variants/derivatives, as long as the resulting molecule retains a desired level of activity as described herein. For example, the recombinant constructs may also contain, in addition to those disclosed herein, other suitable mutations or alterations such as various additional amino acid substitutions, which may be conservative or non-conservative amino acid substitutions, and/or additions to or deletions from the sequence, may be included in and tolerated by the recombinant enzymes, while still allowing the further mutated recombinants to retain a desired or useful level of activity. Exemplary additional mutations include but are not limited to: changes which introduce or eliminate sequences susceptible to proteolysis; addition of various "tagging" sequences which may be used to identify and/or to isolate the sequences, e.g. His tags, HA tag etc., changes which increase or decrease solubility; incorporation of one or more so-called "non-natural" amino acids; additions or deletions of amino acids at either terminus or internally (e.g. typically about 1-20 amino acids); etc. All such possible variants of derivatives of the constructs disclosed herein are encompassed by the present invention. The constructs described herein may also be associated with other moieties. The association can be covalent or non-covalent, and can be, for example, via a terminal amino acid linker (such as Lys or Cys) or a chemical coupling agent. Levels of similarity and/or identity between such variant sequences and the sequences disclosed herein are generally at least about 50, 55, 60, 65, 70, 75, 80, 85, 90 95, or greater %, e.g. 96, 97, 98 or 99%.

In addition, modifications of the particular OspC types selected to make up the L5/H5 epitope pairs in disclosed chimeritopes are also encompassed, e.g. one or more epitope types may be substituted and/or deleted and/or added to the sequence, so long as sufficient antibody reactivity is retained to detect naturally occurring antibodies to each OspC type included in the construct if they are present (when used in a diagnostic), or to elicit an adequate immune response (when used in a vaccine).

Nucleic Acids and Cells

Nucleic acids which encode the amino acid sequences described herein are also encompassed, as are vectors and cells comprising the nucleic acids. "Nucleic acids" include RNA (e.g. mRNA), DNA, cDNA, etc. as well as hybrids thereof. Vectors housing such nucleic acids are also provided. The term "vector" is used to refer to a carrier nucleic acid molecule into which a nucleic acid sequence can be inserted, e.g. for introduction into a cell where it can be replicated. The vectors may be, for example, expression vectors which produce proteins through the transcription of the vector's insert followed by translation of the mRNA produced, or transcription-only vectors that produce mRNA. Viral vectors include those that are suitable for production of the constructs, e.g. in a cell, or in an organism that is being vaccinated, etc. Suitable viral vectors include but are not limited to adenoviral vectors, retrovirus vectors, herpes simplex viral vectors, etc.

The invention also encompasses cells which are transformed to contain vectors comprising one or more nucleic acids which encode the antigens described herein, e.g. for production of the antigens described herein. Exemplary expression systems include but are not limited to bacterial systems (e.g. *Escherichia coli, Corynebacterium, Pseudomonas fluorescens*, etc.); and eukaryotic systems (e.g. *Saccharomyces cerevisiae, Pichia Pastoris*, filamentous fungi, *Baculovirus*-infected cells, non-lytic insect cell expression, *Leishmania*, various plant systems (e.g. tobacco), various mammalian systems, various cell-free systems, etc.).

The Assays

The invention provides assays (systems) and methods for use to i) diagnose Lyme disease infection; and to ii) determine the stage of infection, e.g. early stage, late stage, and, optionally, mid-stage Lyme disease. The assays generally involve testing of a suitable biological sample from a subject known or suspected to have been exposed to a Lyme disease spirochete or a tick species that carries these pathogens. The subject may or may not have one or more symptoms of Lyme disease. Alternatively, the test may be carried out as part of a routine diagnostic for individuals that have entered or live in endemic regions of Lyme disease. In addition, the tests may be used to assess whether or not a person or animal (canines for example) has previously received an ospC or OspE based vaccine. Testing such individuals or animals will allow for an assessment of their immune status (i.e., do they have sufficient circulating antibody titers that would provide protection). In the case of canines, the test could also assess the immune status of dogs that were vaccinated with bacterin vaccines (i.e., vaccines that consist of whole cell lysates of the Lyme disease spirochetes that have been inactivated). The test would therefore allow for an assessment of the success of vaccination. In addition, the subject may be a control subject that is known to not be infected. The subjects that are tested are generally vertebrates, and may be mammals, for example, humans, canines (domestic dogs, coyotes, wolves, etc.), cats, "wild" animals such as deer, raccoons, mice squirrels, raccoons, shrews, chipmunks, and/or animals located in protected areas such as preserves and zoos. The subjects may also be birds. Any subject of any species that is susceptible to contracting or harboring the causative agent of Lyme disease (*Borrelia*) may be effectively tested for the presence of infection using the assays and methods described herein.

The biological sample that is assayed is, for example, blood, serum, cerebrospinal fluid, and or synovial fluid, etc. However, typically, the biological sample is a blood sample since obtaining blood is less invasive than obtaining other bodily fluids and the associated procedures are less prone to lead to adverse events.

Generally, to conduct an assay, constructs representing both early and late stage disease are utilized, although this need not always be the case, as single-antigen, stand-alone assays using any of the constructs described herein are also encompassed, i.e. the use of the antigens in single-antigen assays is not excluded. However, typically a combination of early and late stage chimeritopes (e.g. at least one of each)

are exposed to the suitable biological sample from a subject that is being tested. The use of multiple proteins is usually the case if the goal is to differentiate different stages of infection.

The assay involves exposing an aliquot or portion of the sample to one or more of the antigenic constructs described herein (i.e. contacting the sample with one or more chimeritopes) and detecting the formation of antibody-antigen complexes between antibodies in the sample (if any) and the antigenic construct(s). Thus, at least one "early stage" OspC construct and at least one "late stage" OspE construct are typically utilized. For example from about 1 to about 5 of each type of construct may be utilized. In some aspects, one early stage and two late stage constructs are employed, e.g. late stage constructs that represent both major OspE proteins that are commonly found in infected individuals. Exposure to the constructs is generally "one type at a time" e.g. each type of construct (early stage or later stage) is exposed to an aliquot or a portion of the sample in a single, separate reaction, with a plurality of single, separate reactions being run side-by-side. However, the use of multiple constructs (especially two or more constructs of the same stage, such as two late stage constructs) is also encompassed. In addition, single chimeric constructs comprising both early and late stage antigens are also encompassed, and in this case, a single reaction may be employed. Detection of a complex indicates the presence of infection and the absence of infection is indicated if no complex is detected.

The concentration of each construct that is used depends on the nature of the assay (e.g. how the antibody-antigen complexes are detected) but is sufficient to result in a detectable amount of complex, either directly (e.g. by gel electrophoresis, etc.) or indirectly, (e.g. by detection of a detectable label that is attached to the complex). Generally, however, the amount of each construct that is used in the assay is in the range of from about 100 ng to 1 ug per assay. For example when the proteins are used in an ELISA format the coating amount of protein is typically 200 ng per well, while for an immunoblot or lateral flow format, up to a microgram per construct might be preferable for each lane or strip.

To conduct an assay, either heterogeneous (one binding partner is immobilized) or homogenous (both binding partners are in solution) approaches may be utilized. The components of a reaction mix, their interaction with each other, and the means of detection of the complexes is dependent on the overall assay format that is employed. Many are known in the art, [e.g. see, for example, Kim and Herr, Biomicrofluidics. 2013 July; 7(4): 041501); Harlow and Lane, Antibodies: A Laboratory Manual, Cold Spring Harbor Laboratory (1988); U.S. Pat. Nos. 9,040,233 and 9,063,150, the complete contents of each of which are incorporated herein by reference]. Exemplary assays are or involve techniques which include but are not limited to: homogeneous reactions involving complex precipitation; direct binding assays involving Western blotting and detection with secondary antibodies linked to an agent such as alkaline phosphatase, horseradish peroxidase, p-nitrophenyl phosphatase, etc.; various radioimmunoassays; magnetic immunoassays, isoelectric focusing (IEF); ELISAs (Enzyme-Linked Immunosorbent Assays), microfluidic immunoassays, in which antigen or antibody is immobilized inside microchannels; surround optical fiber immunoassays (SOFIAs); lateral flow immunochromatographic assays; immunoassay cassettes, crosslinking and denaturing or non-denaturing PAGE and further gel visualization, chromatography (size exclusion), surface plasmon resonance, etc.

Generally, a technique involving immobilization is used and typically it is the constructs that are immobilized on a substrate, although other assay formats are not excluded. Suitable substrates for immobilization are known in the art, e.g. the surfaces of microwell plates, membranes (e.g. Immobilon®, nitrocellulose, etc.) which may be in the form of a strip, beads (e.g. latex, magnetic, etc.), glass, silicon or metal surfaces, etc. The invention thus also comprises substrates comprising the constructs described herein. The constructs are generally deposited on a surface of the substrate, at spaced-apart intervals. The substrate may be, for example, a membrane strip or ELISA plate well that is used in an assay. Accordingly, the invention also provides devices for detecting *Borrelia* OspC antibodies and OspE antibodies in a biological sample, e.g. as a part of an assay kit. The devices generally comprising a substrate and an antigenic polypeptide comprising two or more OspC loop 5/helix 5 pairs from a plurality of OspC types and at least one recombinant OspE mutant that does not bind factor H immobilized on the substrate. In some aspects, the substrate is a strip and the antigenic polypeptide and the at least one recombinant OspE mutant are immobilized at separate, spaced apart locations on the strip. In other aspects, the substrate is a multiwell plate and the antigenic polypeptide and the at least one recombinant OspE mutant are immobilized in separate wells of the multiwell plate. If a plurality of recombinant OspE mutant are used, each is typically immobilized at a separate location (e.g. at a separate location on a strip, or in a separate well, etc).

Generally, detection of antigen-antibody complexes involves the use of detectable labels. For example, the constructs (or the antibodies in the sample, see U.S. Pat. No. 9,063,150) may be labeled with detectable labels which remain attached to the complex, e.g. after removal of excess, unreacted construct and/or serum. Alternatively, detectable labels may be introduced after the complex is formed, e.g. by the use of labeled secondary and/or tertiary antibodies that bind to the complexes after removal of excess, unreacted construct and/or serum. Exemplary detectable labels include but are not limited to: radioactive labels, non-radioactive isotopic labels, fluorescent labels, chemiluminescent labels, paramagnetic labels, enzyme labels and colorimetric labels.

In one exemplary aspect, the assay is an ELISA assay. In this exemplary assay, separate wells of a multiwell plate are coated with early and late stage antigenic constructs, e.g. with at least one OspC derived early stage chimeritope and at least one OspE derived late stage protein, and the constructs are allowed to bind to the well surfaces. In one aspect, one early antigen and two late antigens are used. The proteins are allowed to bind and the wells are washed to remove unbound antigen and bound antigen is blocked with a blocking agent to prevent non-specific antibody binding. Diluted serum (typically a 1:100 to 1:500 dilution) from each subject being tested is added to the wells and kept in the wells for a period of time sufficient for antibodies in the sample, if any, to bind to the test antigens. For example, the test samples may be incubated for at least one hour, or for several hours, or even overnight. The serum is then removed (e.g. by aspiration), the plates are washed to remove excess sample, and bound IgG and or IgM is detected by adding to the wells an anti-IgG or anti-IgM antibody that is specific for the mammalian species being tested, e.g. is specific for humans, for dogs, etc. Typically, the anti-IgG and or anti-IgM antibody is labeled with a detectable (e.g. fluorescent) label. Unbound anti-IgG and or anti-IgM antibody is removed from the wells (e.g. by aspiration) and the wells are washed to remove unbound anti-IgG and or anti-IgM antibody. The level of antibody that remains bound to the wells is then determined, e.g. using an ELISA plate reader that detects absorbance or fluorescence from bound secondary antibody.

Kits containing reagents necessary for carrying out the assays are also encompassed by the present disclosure. Such kits may contain, for example, chimeritopes in a suitable form such as a solid form (e.g. freeze-dried), or concentrated in solution, etc., for use in preparing an assay, as well as other reagents such as buffers, control samples, secondary and tertiary antibodies that are labeled or ready to label, labeling agents, instructions for use, etc. Alternatively, the kit may comprise a substrate such as a multiwell plate, membrane or other solid support to which the constructs are already bound and such other reagents as are necessary to conduct the assay.

If antibody to at least one antigenic construct as described herein is detected in a sample, then the subject from whom the sample was obtained is diagnosed as being or having been infected by a Lyme disease spirochete. If both early and late stage constructs are employed in the assay, then the subject is diagnosed as having an early stage infection if the amount of antibody to the early stage construct exceeds the amount of antibody to the late stage construct, and the subject is diagnosed as having a late stage infection if the amount of antibody to the late stage construct exceeds the amount of antibody to the early stage construct. In some aspects, the relative amounts of early to late stage antigen are calculated and thresholds are established to define early, middle and late stage infection.

An exemplary data interpretation, which should not be interpreted as limiting in any way, is as follows:

1. A diagnosis of "positive" or "infected" may be made if the total (combined) value (quantity) or concentration (e.g. ELISA units, fluorescence units or absorbance values read) for a serum sample screened against one OspC chimeritope protein (A12CF for example), one BBN38 mutant protein (BBN38-13 for example) and one BBL39 mutant protein (BBL39-9 for example) is at least about 1.2 fold greater than the total ELISA units, fluorescence units or absorbance values of a suitable known negative control sample, e.g. a sample of pooled serum from comparable but uninfected subjects of the same species, when screened against the same antigens under the same conditions. For example, samples of pooled human serum are commercially available and may be used as a negative control.
2. A diagnosis of early infection may be made when the ratio of ELISA units, fluorescence units or absorbance values obtained using an OspC chimeritope (A12CF for example) to the ELISA units, fluorescence units or absorbance values obtained using an OspE mutant (BBN38-13 for example, BBN39-9 for example, or combined BBN38-13 and BBN39-9 for example) is, for example, equal to or greater than about 1.25.
3. A diagnosis of mid-stage infection may be made when the ratio of ELISA units, fluorescence units or absorbance values obtained using an OspC chimeritope (A12CF for example) to the ELISA units, fluorescence units or absorbance values obtained using an OspE mutant (BBN38-13 for example, BBN39-9 for example, or combined BBN38-13 and BBN39-9 for example) is, for example, greater than about 0.75 and less than about 1.25.
4. A diagnosis of late stage infection may be made when the ratio of ELISA units, fluorescence units or absorbance values obtained using an OspC chimeritope (A12CF for example) to the ELISA units, fluorescence units or absorbance values obtained using an OspE mutant (BBN38-13 for example, BBN39-9 for example, or combined BBN38-13 and BBN39-9 for example) is, for example, equal to or less than about 0.75.

Those of skill in the art will recognize that the absolute threshold or cut-off values described above are only exemplary in nature. These values will vary, depending on the type of subject (e.g. human or canine), on attributes of an individual subject, the exact sample of pooled serum that is used as a control, and the identity of the constructs that are used in the assay, and the nature of the assay itself. However, generally if a quantity of OspC antibodies that is measured or detected is greater than a quantity of OspE antibodies, then a practitioner of the method will conclude that the *Borrelia* infection is an early stage infection; and if a quantity of OspC antibodies is less than a quantity of OspE antibodies, then the practitioner would conclude that the *Borrelia* infection is a late stage infection.

Compositions

Compositions for Use in Assays

The present invention provides compositions of and compositions comprising the constructs described herein as well as nucleic acid sequences encoding such antigens. The compositions may be or may include a polypeptide comprising SEQ ID NO: 2 (RM9A61) or a variant thereof having at least 90% amino acid sequence identity or similarity to SEQ ID NO: 2; SEQ ID NO: 4 (EurAs9v2) or a variant thereof having at least 90% amino acid sequence identity or similarity to SEQ ID NO: 4; and/or a recombinant OspE mutant that does not bind factor H, with a caveat that if said recombinant OspE mutant that does not bind factor H is a BBL-39 polypeptide, then the polypeptide does not have an amino acid sequence that is identical to SEQ ID NOS: 11-26. For example, the recombinant OspE mutant that does not bind factor H may be SEQ ID NO: 29 (BBN38-13) or a variant thereof having at least 90% amino acid sequence identity or similarity to SEQ ID NO: 29, or SEQ ID NO: 31 (BBN38-37) or a variant thereof having at least 90% amino acid sequence identity or similarity to SEQ ID NO: 31. The compositions may be solid, e.g. salts and/or reconstitutable powders (e.g. lyophilized preparations) comprising at least one polypeptide construct as described herein. In other aspects, a composition comprises at least one polypeptide construct as described herein, dissolved or dispersed in a liquid vehicle. The liquid vehicle may be aqueous or oil-based. If aqueous based, the compositions may be solutions comprising one or more constructs and a medium or buffer that is suitable for carrying out the assays described herein. The compositions may comprise one or more than one of any of the constructs described herein. For example, exemplary buffers include carbonate buffers which are frequently employed in ELISA assays.

Immunogeninc and Preventative and/or Therapeutic Vaccine Compositions

In another aspect, vaccines and immunogenic compositions are provided for use in eliciting an immune response and/or vaccinating a subject against Lyme disease are provided, as are methods of vaccinating or immunizing a subject against Lyme disease. In other aspects, the compositions are used as a therapeutic vaccine to treat individuals or animals that are already infected with *Borrelia*. The compositions include one or more isolated and/or substantially purified antigenic constructs as described herein, or nucleic acid sequences encoding such antigens, and a pharmacologically suitable carrier. Exemplary constructs which may be included in such compositions include but are not limited to: RM9A61 (SEQ ID NO: 2) and variants thereof; EurAs9v21 (SEQ ID NO: 4) and variants thereof; the BBN-38 constructs in SEQ ID NOS: 28-35, and variants thereof; and BBN-39 constructs as described herein, with the caveat that the sequences are not identical to SEQ ID NOS: 11-26.

The preparation of such compositions is known to those of skill in the art. Typically, such compositions are prepared either as liquid solutions or suspensions, however solid forms such as tablets, pills, powders, food material (bait vaccine) and the like are also contemplated. Solid forms suitable for solution in, or suspension in, liquids prior to administration may also be prepared. The preparation may also be emulsified. The liquids may be aqueous or oil-based suspensions or solutions. The active ingredients may be mixed with excipients which are pharmaceutically acceptable and compatible with the active ingredients, e.g. pharmaceutically acceptable salts. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain one or more adjuvants. If it is desired to administer an oral form of the composition, various thickeners, flavorings, diluents, nutrients, emulsifiers, dispersing aids or binders and the like may be added. The composition may contain any such additional ingredients so as to provide the composition in a desirable form suitable for administration. The final amount of antigen or encoding nucleic acid in the formulations may vary. However, in general, the amount in the formulations will be from about 1-99%. Still other suitable formulations for use in the present invention can be found, for example in Remington's Pharmaceutical Sciences, Philadelphia, Pa., 19th ed. (1995). In addition, other peptides and/or polypeptides suitable for immunizing against Lyme disease or other diseases of interest (e.g. multivalent vaccines) may also be present in the compositions. In addition, the vaccines may also be used therapeutically to treat an actively infected individual or mammal.

Some examples of materials which can serve as pharmaceutically acceptable carriers include, but are not limited to, ion exchangers, alum, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions may be administered in vivo by any suitable route including but not limited to: inoculation or injection (e.g. intravenous, intraperitoneal, intramuscular, subcutaneous, and the like), by inhalation (e.g. as a mist or spray), orally (e.g. as a pill, capsule, liquid, formulated into food etc.) and the like. In preferred embodiments, the mode of administration is by injection. In addition, the compositions may be administered in conjunction with other modalities such with other antigens or vaccinogens for diseases other than Lyme disease, i.e. the present antigens may be formulated into a combination vaccine. For example, for animal vaccinations, the antigens of the invention may be administered in combination with one or more exemplary antigens including but not limited to those for: human granulocytic anaplasmosis, ehrlichiosis, babesiosis, Powassan virus, tick borne encephalitis, relapsing fever caused by *Borrelia* species, West Nile virus, distemper, hepatitis, parvovirus, parainfluenza, rabies, etc. For human vaccines, the antigens of the invention may be administered in combination with antigens for one or more exemplary antigens which include but are not limited those for: human granulocytic anaplasmosis, ehrlichiosis, babesiosis, Powassan virus, tick borne encephalitis, relapsing fever caused by *Borrelia* species, West Nile virus, polio, diphtheria, pertussis, tetanus, measles, mumps, rubella, influenza, hepatitis, rotavirus, meningitis, etc.

The subjects that are immunized as described herein are generally vertebrates, and may be mammals, for example, humans, non-human primates, canines (domestic dogs, coyotes, wolves, etc.), cats, horses, "wild" animals such as deer, raccoons, mice, squirrels, raccoons, shrews, chipmunks, and/or animals located in privately owned land, protected areas such as preserves and zoos. The subjects may also be birds. Any subject of any species that is susceptible to contracting or harboring the causative agents of Lyme disease (pathogenic species of the *Borrelia burgdorferi* sensu lato complex) may be immunized as described herein.

The compositions can be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity.

The vaccine compositions of the invention are administered to a subject in order to prevent the occurrence of, or optionally, to treat, one or more symptoms of Lyme disease. Those of skill in the art will recognize that in some cases, Lyme disease symptoms are entirely prevented so that complete protection is achieved. However, much benefit can accrue even if symptoms are not completely eradicated but are instead lessened, or ameliorated, or the duration of symptoms is shortened, compared to symptoms of unvaccinated individuals.

In preferred embodiments, the antigenic construct is RM9A61, a recombinant BBL39 mutant and/or a recombinant BBN38 mutant when the subject is a human; and the antigenic construct is A12CF, a recombinant BBL39 mutant or a recombinant BBN38 mutant if the subject if a dog or other non-human animal that can carry or become infected with Lyme disease spirochetes. Compositions comprising RM9A61 may contain one or more of the other constructs described herein.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indictates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Figure 6:
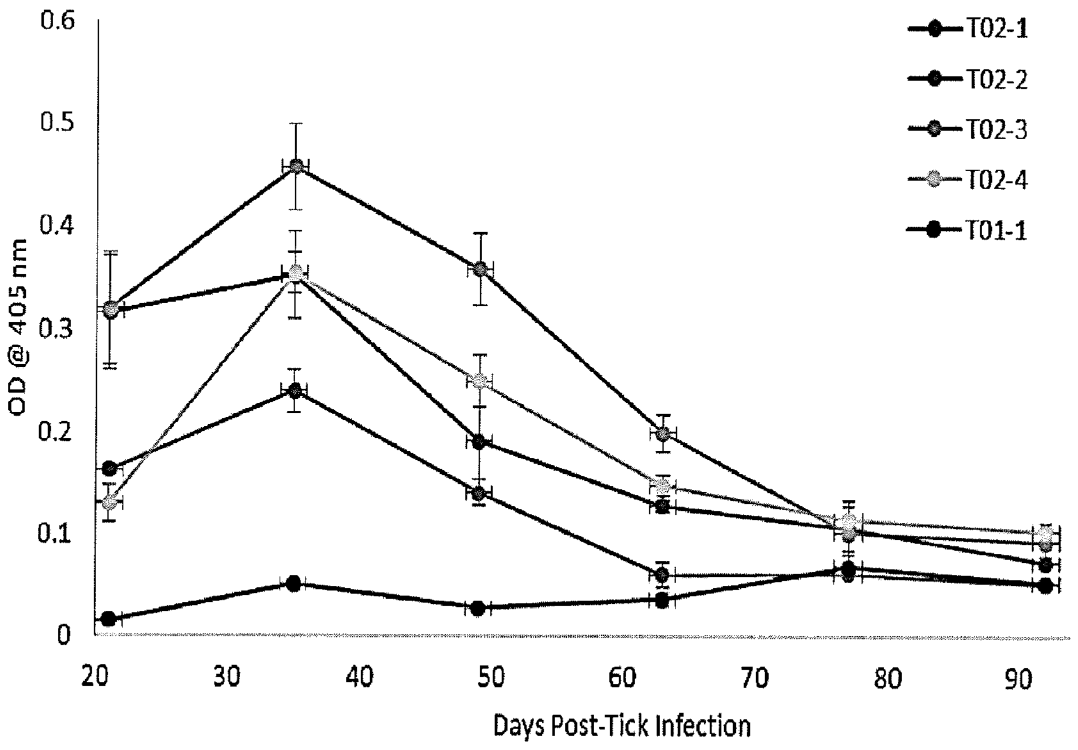
FIG. 6. The RM9A61 diagnostic antigen detects antibodies that develop and are abundant during early infection but are absent or present at significantly reduced levels during late infection. A series of purposed bred beagles (T02-1 though T02-4) were infected by infestation with Lyme disease infected ticks collected from the Northeast. Serum was collected from each dog at the time points indicated on the graph and tested by ELISA for antibodies that bind to RM9A61. A significant response was detected as early as day 21 post tick exposure. By day 75, the Ab response to RM9A61 waned to near baseline levels. Dog T01-1 was one of several negative control dogs that were not exposed to infected ticks. The data with dog T01-1 is representative of all negative control dogs that were tested.

The ability of the representative OspC chimeritopes described herein to detect IgG and or IgM antibody in humans and IgG and or IgM in canines in a highly specific fashion during early infection has been rigorously demonstrated. Focusing first on analyses of anti-OspC directed immune responses in canines, in one series of experiments purpose bred beagles were infected with field collected ticks from the Northeast and serum was harvested over the course of infection (day 0 to day 92) (FIG. 6). Ab in the serum of infected dogs that recognizes RM9A61 (as well as A12CF, data not shown) can be readily detected at day 21 post tick infection using in this instance an ELISA format. In addition, purpose bred beagles that had never been exposed to ticks or Lyme disease spirochetes were also screened (n=50). In no sample was Ab detected that recognized the OspC chimeritopes, demonstrating the specificity of the antigen and the assay. The superiority of the chimeritopes in detecting early antibody compared to that of other commonly employed approaches or tests such as western blotting (with cell lysates as the immobilized antigen) and the commercially available SNAP4Dx test was also demonstrated (Table 1). In Table 1, the percentage of dogs that tested positive at each time point with each assay are shown as a percentage. Reliable detection of anti-*Borrelia burgdorferi* Ab by western blotting or SNAP4Dx could only be achieved after a longer infection time frame. BBL39 and BBN38 mutants are also highly effective for diagnosing late stage disease (not shown).

TABLE 1

RM9A61 and BBL39-9 when used together can detect infection earlier than the commercially available SNAP 4 Dx test (IDEXX Laboratories).

| Serum collected (days Post-Infection) | SNAP 4Dx Test | RM9A61 | BBL39-9 | RM9A61 + BBL39-9 |
|---|---|---|---|---|
| 21 | 0% | 100% | 0% | 100% |
| 35 | 40% | 100% | 80% | 100% |
| 49 | 100% | 90% | 100% | 100% |
| 63 | 100% | 80% | 100% | 100% |
| 77 | 100% | 40% | 100% | 100% |
| 92 | 100% | 40% | 100% | 100% |

Figure 7:
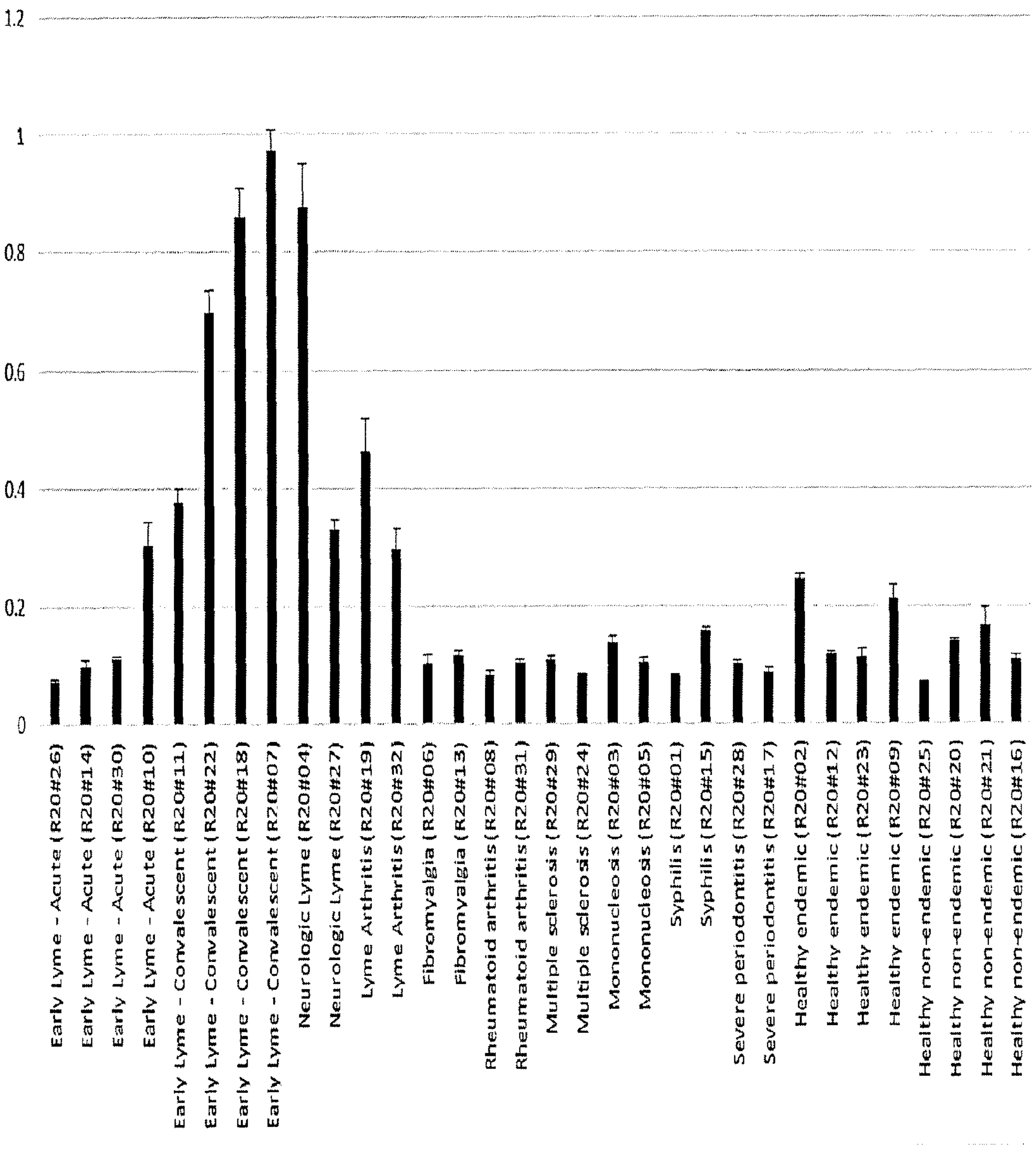
FIG. 7. Demonstration that RM9A61 detects Lyme disease specific human IgG and IgM. A panel of serum samples provided by the Centers for Disease Control and Prevention were screened to assess the specificity of the RM9A61 diagnostic antigen using an ELISA based assay. A high degree of specificity was observed. RM9A61 readily detected IgG and or IgM Ab in most Lyme disease patients. Importantly there was only minimal and low level cross reactivity of serum collected from patients with diseases that clinically mimic one or more of the clinical manifestations of Lyme disease (these diseases are indicated in the figure).

Screening of human serum panels provided by the Centers for Disease Control (CDC) also demonstrated high specificity and sensitivity of the chimeritopes. In humans, the chimeritopes were effective at detecting both IgG and IgM or both (FIG. 7).

These data demonstrate the superior ability of the OspC chimeritopes of the invention to detect infection during early stage disease.

Example 2. Exemplary OspE Mutants that do not Bind to Factor H

Mutants were generated by random mutagenesis of the wild type BBL39 gene. The genes were then cloned into an expression vector and recombinant protein was generated for each mutant in *E. coli*. The proteins were then tested for factor H (FH) binding using an affinity ligand binding immunoblot format and for the ability to bind to antibody (referred to as infection antibody or iAb) that develops to BBL39 during natural infection in mice. The serum was obtained from mice that were infected with *Borrelia burgdorferi* strain B31. FIG. 8 depicts the aligned sequences of BBL39 variants (using a designation that omits "BB"). Their ability to bind FH and or iAb is indicated to the right. The total number of amino acid changes in each mutant protein is listed to the right (#m). The data demonstrate that the BBL39 residues required for FH and iAb binding are not concentrated in a defined domain of region of but rather are dispersed throughout the protein. The results indicate that the FH binding site is discontinuous and that the iAb binding site is conformational in form. The ability to generate a recombinant BBL39 protein that does not bind FH is important because such a protein will have enhanced ability to bind to antibody to BBL39 that develops during infection. Since FH cannot bind it will not interfere or compete with antibody for binding to BBL39.

Any OspE based mutant, including the exemplary mutants shown in FIG. 8, may be used in the practice of the invention, as long as the mutant has the ability to bind to anti-OspE antibodies elicited during infection but does not have the ability to bind to FH.

Example 3. Additional Exemplary OspE (BBN38) Proteins that do not Bind Factor H (FH)

Mutants were generated by random mutagenesis of the wild type BBN38 gene. The genes were then cloned into an expression vector and recombinant protein was generated for each mutant in *E. coli*. The proteins were then tested for factor H (FH) binding using an affinity ligand binding immunoblot format and for the ability to bind to antibody (referred to as infection antibody or iAb) that develops to BBN38 during natural infection in mice. The serum was obtained from mice that were infected with *Borrelia burgdorferi* strain B31. FIG. 9 depicts the aligned sequences of BBN38 variants (using a designation that omits "BB"). Their ability to bind FH and or iAb is indicated to the right. The total number of amino acid changes in each mutant protein is listed to the right (#m). The data demonstrate that the BBN38 residues required for FH and iAb binding are not localized in a defined domain of region of but rather are dispersed throughout the protein. The results suggest that the FH binding site is discontinuous and that the iAb binding site is conformational in form. The ability to generate a recombinant BBL39 protein that does not bind FH is important because such a protein will have enhanced ability to bind to antibody to BBN38 that develops during infection. Since FH cannot bind it will not interfere or compete with antibody for binding to BBN38.

Any OspE based mutant, including the exemplary mutants shown in FIG. 9, may be used in the practice of the invention, as long as the mutant has the ability to bind to anti-OspE antibodies elicited during infection but does not have the ability to bind to FH.

Example 4. Mutated OspE Related Proteins that Lack FH Binding Ability have Greater Antibody Detection Sensitivity ELISA analyses comparing the detection sensitivity of mutant BBL39-9 (which lacks FH binding ability) and wild type BBL39 for detecting anti-BBL39 Ab that developed in experimentally infected canines were conducted. Briefly, recombinant wild type BBL39 and mutant BBL39-9 were immobilized in the wells of an ELISA plate and screened with serum collected over time from a dog (T01-1) that was not infected with Lyme disease and from a dog (T04-1) that was infected by tick bite. Serum was collected and screened for antibodies that can recognize BBL39 or BBL39-9.

Figure 10:
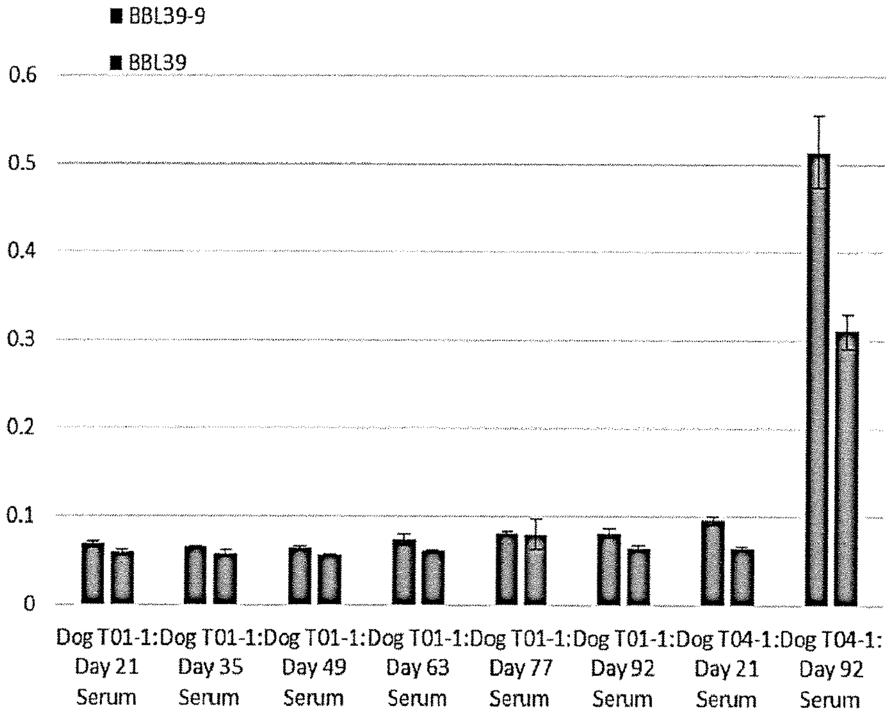
FIG. 10. Demonstration that mutated OspE related proteins that lack FH binding ability have greater antibody detection sensitivity. The data below are representative. Recombinant BBL39 and BBL39-9 were immobilized in the wells of an ELISA plate and incubated with serum collected from representative purpose bred beagles that were infected (T04-1) or were not infected (dog T01-1) with Lyme disease. Serum was collected and screened for antibody that can recognize BBL39 or BBL39-9 (a mutant that lacks the ability to bind FH). The values on the left of the graph indicate Absorbance values at a wavelength of 405 nm. Error bars are shown.

The results are presented in FIG. 10. As can be seen, consistent with the unique ability of OspE proteins to detect late infection, no Ab was detected at day 21 post infection using either protein. However, at day 92, Ab is readily detected by both proteins, but the signal is much greater with BBL39-9 than with BBL39. BBL39-9 improved detection sensitivity by 45% relative to that of the wild type BBL39 protein.

These results demonstrate i) the ability of OspE derived proteins to detect antibodies during late stage Lyme disease infection; and ii) the novel mutated OspE-derived proteins described herein display improved sensitivity compared to wild type OspE. Hence the use of the OspE mutants described herein in diagnostic assays significantly improves sensitivity of the assay.

Figure 11:
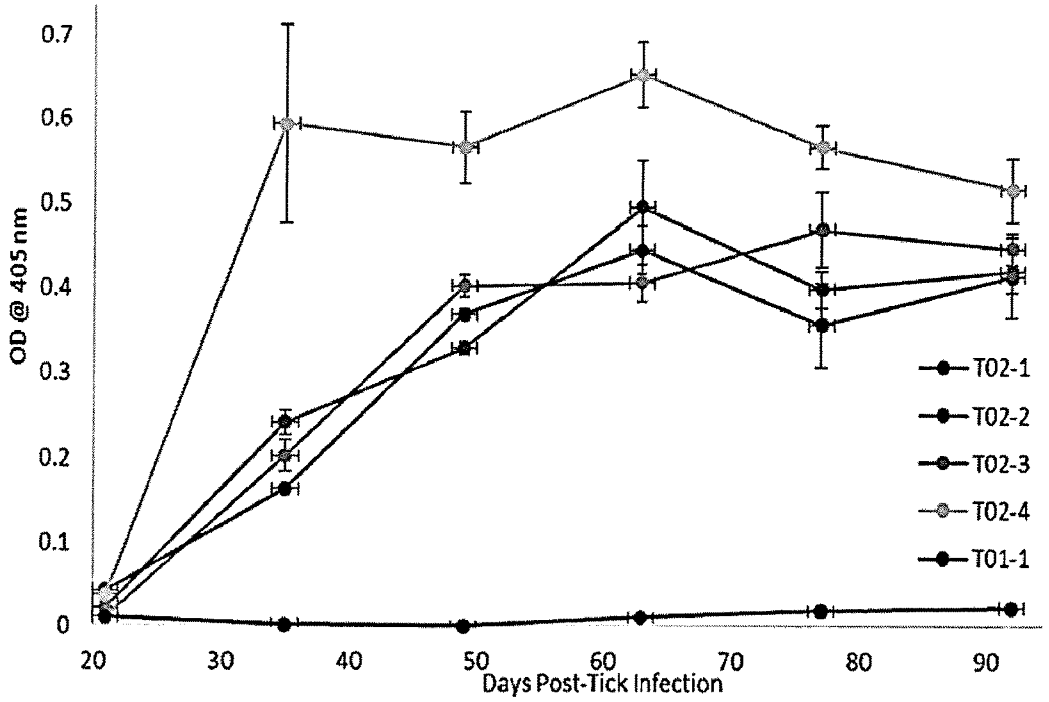
FIG. 11. The BBL39-9 diagnostic antigen detects antibodies that develop specifically during late stage infection. A series of dogs (T02-1 though T02-4) were infected by infestation with Lyme disease infected ticks. Serum was collected at the time points indicated on the graph and tested by ELISA for antibodies that can bind to BBL39-9. Dog T01-1 was a representative negative control dog that was not exposed to infected ticks.

Example 5. Detection of Late Stage Antigens Using the BBL39-9 Diagnostic Antigen The ability of OspE paralogs and mutants to detect antibody that develops during late stage infection was further demonstrated in additional canines, humans and mice. Focusing on the canine studies, a series of dogs (T02-1 though T02-4) were infected by infestation with Lyme disease infected ticks. Serum was collected at the time-points indicated on the graph in FIG. 11 and tested by ELISA for antibodies to BBL39-9 and BBN38. As can be seen, antibodies that recognized one or both of these proteins were specifically detected beginning approximately at day 35 post-tick infestation. No significant Ab levels were detected at day 21 highlighting the unique ability of these proteins to detect Ab that develops during later infection. Ab levels to these proteins remained high throughout the course of infection (day 92). In separate experiments, we demonstrated that Ab that recognizes BBL39-9 could be detected as late as day 497 post-tick infestation (not shown) and that BBL39 and BBN38 can detect infection in humans and mice These results demonstrate that the BBL39-9 diagnostic antigen successfully and reliably detects antibodies that develop during late stage *Borrelia* infection, but which are absent during early infection. Thus, these diagnostic antigens are stage specific for late stage Lyme disease.

Example 6

Determination of the level of non-specific Ab in healthy canines. In order to determine the appropriate threshold level of specific antibody that should be used to make a positive diagnosis of Lyme disease we first established the normal level of non-specific antibody in healthy purpose bred laboratory beagle (FIG. 15). By comparing this value with the levels of specific antibody that are detected in experimentally infected dogs we established that a positive diagnosis requires antibody levels that are 1.2 fold greater than background. The level of non-specific antibody in healthy dogs is low with only minimal variation among the extensive panel of 78 dogs tested.

Example 7

With the exception of the analyses of the human serum samples, other data presented in this application were obtained using serum samples primarily from experimentally infected dogs. In FIG. 16 data are presented demonstrating the detection of antibody in canine patient serum that recognizes A12CF, BBN38 and BBL39-9. The results presented demonstrate the high sensitivity of these proteins for detecting Lyme disease specific antibody. The data demonstrate that the A12CF, BBN38 and BBL39-9 assay has significantly greater sensitivity than the SNAP4Dx test. Eleven serum samples that were weakly positive or negative with the SNAP4Dx test were strongly positive with the A12CF, BBN38 and BBL39-9 assay. As expected for canine patients, the data demonstrate that the majority of dogs have middle or late stage disease. This is expected because dogs are not typically presented by their owners at a clinic until arthritis and other late stage manifestations are evident.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A recombinant polypeptide comprising SEQ ID NO: 2 (RM9A61) or a variant thereof having at least 90% amino acid sequence identity or similarity to SEQ ID NO: 2; or SEQ ID NO: 4 (EurAs9v2) or a variant thereof having at least 90% amino acid sequence identity or similarity to SEQ ID NO: 4.

2. A reconstitutable powder comprising a recombinant polypeptide of claim 1.

3. A composition comprising a recombinant polypeptide of claim 1, and a liquid vehicle.

4. A vaccine or immunogenic composition comprising one or more antigenic recombinant polypeptides selected from the group consisting of: SEQ ID NO: 2 (RM9A61) or a variant thereof having at least 90% amino acid sequence identity or similarity to SEQ ID NO: 2; and SEQ ID NO: 4 (EurAs9v2) or a variant thereof having at least 90% amino acid sequence identity or similarity to SEQ ID NO: 4; and a physiologically compatible carrier.

5. The vaccine or immunogenic composition of claim 4 comprising SEQ ID NO: 2 (RM9A61) or a variant thereof having at least 95% amino acid sequence identity or similarity to SEQ ID NO: 2; SEQ ID NO: 4 (EurAs9v2) or a variant thereof having at least 95% amino acid sequence identity or similarity to SEQ ID NO: 4; and a physiologically compatible carrier.

6. The recombinant polypeptide of claim 1, wherein the variant of SEQ ID NO: 4 (EurAs9v2) has at least 95% amino acid sequence identity or similarity to SEQ ID NO: 4.

* * * * *

SEQUENCE LISTING

```
<160> NUMBER OF SEQ ID NOS: 36

<210> SEQ ID NO 1
<211> LENGTH: 488
<212> TYPE: PRT
<213> ORGANISM: Artificial Sequence
<220> FEATURE:
<223> OTHER INFORMATION: Synthetic chimeric antigenic polypeptide
      comprising OspC epitopes

<400> SEQUENCE: 1

Ala Lys Leu Lys Gly Glu His Thr Asp Leu Gly Lys Glu Gly Val Thr
1               5                   10                  15

Lys Gly Ala Asp Glu Leu Glu Lys Leu Phe Glu Ser Val Lys Asn Leu
            20                  25                  30

Ser Lys Ala Ala Lys Glu Met Leu Thr Asn Ser Val Lys Glu Ser Glu
        35                  40                  45

Lys Phe Ala Gly Lys Leu Lys Asn Glu His Ala Ser Leu Gly Lys Lys
    50                  55                  60

Asp Ala Thr Lys Gly Ala Lys Glu Leu Lys Asp Leu Ser Asp Ser Val
65                  70                  75                  80

Glu Ser Leu Val Lys Ala Ser Asp Asp Phe Thr Lys Lys Leu Gln Ser
                85                  90                  95

Ser His Ala Gln Leu Gly Val Ala Gly Gly Ala Thr Thr Ala Asp Glu
            100                 105                 110

Leu Glu Lys Leu Phe Lys Ser Val Glu Ser Leu Ala Lys Ala Ala Gln
        115                 120                 125

Asp Ala Leu Ala Asn Ser Val Asn Glu Leu Thr Ser Lys Lys Leu Lys
    130                 135                 140
```

-continued

```
Glu Lys His Thr Asp Leu Gly Lys Lys Asp Ala Thr Ala Ala Glu Leu
145                 150                 155                 160

Glu Lys Leu Phe Glu Ser Val Glu Asn Leu Ala Lys Ala Ala Lys Glu
                165                 170                 175

Met Leu Ser Asn Ser Asn Lys Ala Phe Thr Asp Lys Leu Lys Ser Ser
            180                 185                 190

His Ala Glu Leu Gly Ile Ala Asn Gly Ala Ala Thr Lys Gly Ala Gln
        195                 200                 205

Glu Leu Glu Lys Leu Phe Glu Ser Val Lys Asn Leu Ser Lys Ala Ala
    210                 215                 220

Gln Glu Thr Leu Asn Asn Ser Val Lys Glu Ser Glu Ser Phe Thr Lys
225                 230                 235                 240

Lys Leu Ser Asp Asn Gln Ala Glu Leu Gly Ile Glu Asn Ala Thr Lys
                245                 250                 255

Gly Ala Glu Glu Leu Val Lys Leu Ser Glu Ser Val Ala Gly Leu Leu
            260                 265                 270

Lys Ala Ala Gln Ala Ile Leu Ala Asn Ser Val Lys Glu Leu Thr Ser
        275                 280                 285

Pro Val Val Ala Glu Ser Pro Lys Lys Pro Asn Asn Ser Gly Lys Asp
    290                 295                 300

Gly Asn Thr Ser Ala Asn Ser Ala Asp Glu Ser Val Lys Gly Pro Asn
305                 310                 315                 320

Leu Thr Glu Ile Ser Lys Lys Ile Thr Glu Ser Asn Ala Val Val Leu
                325                 330                 335

Ala Val Lys Glu Ile Glu Thr Leu Leu Ser Ser Ile Asp Glu Leu Ala
            340                 345                 350

Thr Lys Ala Ile Gly Gln Lys Ile Asp Ala Asn Gly Leu Gly Val Gln
        355                 360                 365

Ala Asn Gln Asn Gly Ser Leu Leu Ala Gly Ala Tyr Ala Ile Ser Thr
    370                 375                 380

Leu Ile Thr Gln Lys Leu Ser Ala Leu Asn Ser Glu Asp Leu Lys Glu
385                 390                 395                 400

Lys Val Ala Lys Val Lys Lys Cys Ser Glu Asp Phe Thr Asn Lys Leu
                405                 410                 415

Lys Asn Gly Asn Ala Gln Leu Gly Leu Ala Ala Ala Thr Asp Asp Asn
            420                 425                 430

Ala Lys Ala Ala Ile Leu Lys Thr Asn Gly Thr Asn Asp Lys Gly Ala
        435                 440                 445

Lys Glu Leu Lys Asp Leu Ser Asp Ser Val Glu Ser Leu Val Lys Ala
    450                 455                 460

Ala Gln Val Met Leu Thr Asn Ser Val Lys Glu Leu Thr Ser Pro Val
465                 470                 475                 480

Val Ala Glu Ser Pro Lys Lys Pro
                485
```

```
<210> SEQ ID NO 2
<211> LENGTH: 612
<212> TYPE: PRT
<213> ORGANISM: Artificial Sequence
<220> FEATURE:
<223> OTHER INFORMATION: Synthetic chimeric antigenic polypeptide
      comprising OspC epitopes

<400> SEQUENCE: 2

Ser Thr Gly Phe Thr Asn Lys Leu Lys Ser Gly His Ala Glu Leu Gly
1               5                   10                  15
```

-continued

```
Pro Val Gly Gly Asn Ala Thr Lys Gly Ala Lys Glu Leu Lys Asp Leu
            20                  25                  30

Ser Glu Ser Val Glu Ala Leu Ala Lys Ala Ala Gln Ala Met Leu Thr
        35                  40                  45

Asn Ser Ser Glu Lys Phe Thr Lys Lys Leu Ser Glu Ser His Ala Asp
    50                  55                  60

Ile Gly Ile Gln Ala Ala Thr Lys Gly Ala Glu Glu Leu Asp Lys Leu
65                  70                  75                  80

Phe Lys Ala Val Glu Asn Leu Ser Lys Ser Glu Glu Phe Ser Thr Lys
                85                  90                  95

Leu Lys Asp Asn His Ala Gln Leu Gly Ile Gln Gly Val Thr Lys Gly
            100                 105                 110

Val Glu Glu Leu Glu Lys Leu Ser Gly Ser Leu Glu Ser Leu Ser Ser
        115                 120                 125

Thr Glu Phe Thr Asn Lys Leu Lys Ser Glu His Ala Val Leu Gly Leu
    130                 135                 140

Asp Asn Leu Thr Lys Gly Ala Ala Glu Leu Glu Lys Leu Phe Lys Ala
145                 150                 155                 160

Val Glu Asn Leu Ser Lys Ala Ala Gln Asp Thr Leu Lys Asn Ala Val
                165                 170                 175

Lys Glu Leu Thr Ser Pro Ile Val Ala Glu Ser Pro Lys Lys Pro Ser
            180                 185                 190

Glu Asp Phe Thr Lys Lys Leu Glu Gly Glu His Ala Gln Leu Gly Ile
        195                 200                 205

Glu Asn Val Thr Ala Ala Glu Leu Glu Lys Leu Phe Lys Ala Val Glu
    210                 215                 220

Asn Leu Ala Lys Ala Ala Lys Glu Met Ser Glu Lys Phe Ala Gly Lys
225                 230                 235                 240

Leu Lys Asn Glu His Ala Ser Leu Gly Lys Lys Asp Ala Thr Lys Gly
                245                 250                 255

Ala Lys Glu Leu Lys Asp Leu Ser Asp Ser Val Glu Ser Leu Val Lys
            260                 265                 270

Ala Ser Asp Asp Phe Thr Lys Lys Leu Gln Ser Ser His Ala Gln Leu
        275                 280                 285

Gly Val Ala Gly Gly Ala Thr Thr Ala Asp Glu Leu Glu Lys Leu Phe
    290                 295                 300

Lys Ser Val Glu Ser Leu Ala Lys Ala Ala Gln Asp Ala Leu Ala Asn
305                 310                 315                 320

Ser Val Asn Glu Leu Thr Ser Lys Lys Leu Lys Glu Lys His Thr Asp
                325                 330                 335

Leu Gly Lys Lys Asp Ala Thr Ala Ala Glu Leu Glu Lys Leu Phe Glu
            340                 345                 350

Ser Val Glu Asn Leu Ala Lys Ala Ala Lys Glu Met Leu Ser Asn Ser
        355                 360                 365

Asn Lys Ala Phe Thr Asp Lys Leu Lys Ser Ser His Ala Glu Leu Gly
    370                 375                 380

Ile Ala Asn Gly Ala Ala Thr Lys Gly Ala Gln Glu Leu Glu Lys Leu
385                 390                 395                 400

Phe Glu Ser Val Lys Asn Leu Ser Lys Ala Ala Gln Glu Thr Leu Asn
                405                 410                 415

Asn Ser Val Lys Glu Asn Asn Ser Gly Lys Asp Gly Asn Thr Ser Ala
            420                 425                 430
```

-continued

```
Asn Ser Ala Asp Glu Ser Val Lys Gly Pro Asn Leu Thr Glu Ile Ser
        435                 440                 445

Lys Lys Ile Thr Asp Ser Asn Ala Val Leu Leu Ala Val Lys Gln Val
    450                 455                 460

Glu Ala Leu Leu Ser Ser Ile Asp Glu Ile Ala Ala Lys Ala Ile Gly
465                 470                 475                 480

Lys Lys Ile His Gln Asn Asn Gly Leu Asp Thr Glu Asn Asn His Asn
                485                 490                 495

Gly Ser Leu Leu Ala Gly Ala Tyr Ala Ile Ser Thr Leu Ile Lys Gln
            500                 505                 510

Lys Leu Asp Gly Leu Lys Asn Glu Gly Leu Lys Glu Lys Ile Asp Ala
        515                 520                 525

Ala Lys Lys Cys Ser Glu Thr Phe Thr Asn Lys Leu Lys Glu Lys His
    530                 535                 540

Thr Asp Leu Gly Lys Glu Gly Val Thr Asp Ala Asp Ala Lys Glu Ala
545                 550                 555                 560

Ile Leu Lys Thr Asn Gly Thr Lys Thr Lys Gly Ala Glu Glu Leu Gly
                565                 570                 575

Lys Leu Phe Glu Ser Val Glu Val Leu Ser Lys Ala Ala Lys Glu Met
            580                 585                 590

Leu Ala Asn Ser Val Lys Glu Leu Thr Ser Pro Val Val Ala Glu Ser
        595                 600                 605

Pro Lys Lys Pro
    610


<210> SEQ ID NO 3
<211> LENGTH: 431
<212> TYPE: PRT
<213> ORGANISM: Artificial Sequence
<220> FEATURE:
<223> OTHER INFORMATION: Synthetic chimeric antigenic polypeptide
      comprising OspC epitopes

<400> SEQUENCE: 3

Ser Glu Thr Phe Thr Asn Lys Leu Lys Glu Lys His Thr Asp Leu Gly
1               5                   10                  15

Lys Glu Gly Val Thr Lys Gly Ala Glu Glu Leu Gly Lys Leu Phe Glu
            20                  25                  30

Ser Val Glu Val Leu Ser Lys Ala Ala Lys Glu Met Leu Ala Asn Ser
        35                  40                  45

Val Lys Glu Leu Thr Ser Ser Glu Glu Phe Ser Thr Lys Leu Lys Asp
    50                  55                  60

Asn His Ala Gln Leu Gly Ile Gln Gly Val Thr Lys Gly Val Glu Glu
65                  70                  75                  80

Leu Glu Lys Leu Ser Gly Ser Leu Glu Ser Leu Ser Ser Glu Asp Phe
                85                  90                  95

Thr Lys Lys Leu Glu Gly Glu His Ala Gln Leu Gly Ile Glu Asn Val
            100                 105                 110

Thr Ala Ala Glu Leu Glu Lys Leu Phe Lys Ala Val Glu Asn Leu Ala
        115                 120                 125

Lys Ala Ala Lys Glu Met Ala Lys Leu Lys Gly Glu His Thr Asp Leu
    130                 135                 140

Gly Lys Glu Gly Val Thr Lys Gly Ala Asp Glu Leu Glu Lys Leu Phe
145                 150                 155                 160

Glu Ser Val Lys Asn Leu Ser Lys Ala Ala Lys Glu Met Leu Thr Asn
                165                 170                 175
```

-continued

```
Ser Lys Glu Ser Glu Lys Phe Ala Gly Lys Leu Lys Asn Glu His Ala
            180                 185                 190

Ser Leu Gly Lys Lys Asp Ala Thr Lys Gly Ala Lys Glu Leu Lys Asp
        195                 200                 205

Leu Ser Asp Ser Val Glu Ser Leu Val Lys Ala Ser Asp Asp Phe Thr
    210                 215                 220

Lys Lys Leu Gln Ser Ser His Ala Gln Leu Gly Val Ala Gly Gly Ala
225                 230                 235                 240

Thr Thr Ala Asp Glu Leu Glu Lys Leu Phe Lys Ser Val Glu Ser Leu
                245                 250                 255

Ala Lys Ala Ala Gln Asp Ala Leu Ala Asn Ser Val Asn Glu Leu Thr
            260                 265                 270

Ser Lys Lys Leu Lys Glu Lys His Thr Asp Leu Gly Lys Lys Asp Ala
        275                 280                 285

Thr Ala Ala Glu Leu Glu Lys Leu Phe Glu Ser Val Glu Asn Leu Ala
    290                 295                 300

Lys Ala Ala Lys Glu Met Leu Ser Asn Ser Asn Lys Ala Phe Thr Asp
305                 310                 315                 320

Lys Leu Lys Ser Ser His Ala Glu Leu Gly Ile Ala Asn Gly Ala Ala
                325                 330                 335

Thr Lys Gly Ala Gln Glu Leu Glu Lys Leu Phe Glu Ser Val Lys Asn
            340                 345                 350

Leu Ser Lys Ala Ala Gln Glu Thr Leu Asn Asn Ser Val Lys Glu Ser
        355                 360                 365

Glu Ser Phe Thr Lys Lys Leu Ser Asp Asn Gln Ala Glu Leu Gly Ile
    370                 375                 380

Glu Asn Ala Thr Lys Gly Ala Glu Glu Leu Val Lys Leu Ser Glu Ser
385                 390                 395                 400

Val Ala Gly Leu Leu Lys Ala Ala Gln Ala Ile Leu Ala Asn Ser Val
                405                 410                 415

Lys Glu Leu Thr Ser Pro Val Val Ala Glu Ser Pro Lys Lys Pro
            420                 425                 430


<210> SEQ ID NO 4
<211> LENGTH: 467
<212> TYPE: PRT
<213> ORGANISM: Artificial Sequence
<220> FEATURE:
<223> OTHER INFORMATION: Synthetic chimeric antigenic polypeptide
      comprising OspC epitopes

<400> SEQUENCE: 4

Ser Glu Lys Phe Thr Thr Lys Leu Lys Asp Ser His Ala Glu Leu Gly
1               5                   10                  15

Ile Gln Ser Val Gln Asp Lys Gly Ala Lys Glu Leu Glu Glu Leu Phe
            20                  25                  30

Lys Ser Leu Glu Ser Leu Ser Lys Ala Ala Gln Ala Ala Leu Thr Asn
        35                  40                  45

Ser Val Lys Glu Leu Thr Asn Ser Asp Lys Phe Thr Lys Lys Leu Thr
    50                  55                  60

Asp Ser His Ala Gln Leu Gly Ala Val Gly Gly Ala Ile Asn Asp Lys
65                  70                  75                  80

Gly Ala Lys Glu Leu Lys Glu Leu Ser Glu Ser Val Glu Ser Leu Ala
                85                  90                  95

Lys Ala Ala Gln Ala Ala Leu Ala Asn Ser Ser Glu Ala Phe Thr Lys
```

-continued

```
            100                 105                 110

Lys Leu Lys Asp Ser Asn Ala Gln Leu Gly Met Gln Asn Gly Ala Ala
        115                 120                 125

Thr Asp Lys Gly Ala Thr Glu Leu Gly Glu Leu Phe Lys Ser Val Glu
    130                 135                 140

Ser Leu Ser Lys Ala Ala Gln Glu Ala Ser Val Ala Phe Thr Ser Lys
145                 150                 155                 160

Leu Lys Ser Ser Asn Ala Gln Leu Gly Val Ala Asn Gly Asn Ala Thr
                165                 170                 175

Asp Lys Gly Ala Lys Glu Leu Lys Glu Leu Phe Glu Ser Val Glu Ser
            180                 185                 190

Leu Ala Lys Ala Ala Gln Ala Ala Leu Val Asn Ser Val Gln Glu Leu
        195                 200                 205

Thr Asn Ser Glu Ala Phe Thr Asn Arg Leu Lys Gly Ser His Ala Gln
    210                 215                 220

Leu Gly Val Ala Ala Ala Thr Asp Lys Gly Ala Lys Glu Leu Lys Asp
225                 230                 235                 240

Leu Ser Glu Ser Val Glu Ser Leu Ala Lys Ala Ala Gln Glu Ala Leu
                245                 250                 255

Ala Asn Ser Val Lys Glu Leu Thr Asn Ser Glu Ala Phe Thr Asn Lys
            260                 265                 270

Leu Lys Glu Lys His Ala Glu Leu Gly Val Asn Gly Gly Asp Thr Thr
        275                 280                 285

Asp Lys Gly Val Glu Asp Leu Glu Lys Leu Ser Glu Ser Val Lys Ser
    290                 295                 300

Leu Leu Lys Ala Ala Gln Ala Ala Leu Ser Asn Ser Ala Ala Phe Thr
305                 310                 315                 320

Lys Lys Leu Gln Asp Gly His Val Asp Leu Gly Lys Thr Asp Val Thr
                325                 330                 335

Thr Lys Gly Ala Thr Glu Leu Glu Glu Leu Phe Lys Ser Val Glu Gly
            340                 345                 350

Leu Val Lys Ala Ala Lys Glu Ala Ser Glu Thr Phe Thr Asn Lys Leu
        355                 360                 365

Lys Glu Lys His Thr Asp Leu Gly Lys Glu Gly Val Thr Lys Gly Ala
    370                 375                 380

Glu Glu Leu Gly Lys Leu Phe Glu Ser Val Glu Val Leu Ser Lys Ala
385                 390                 395                 400

Ala Lys Glu Met Leu Ala Asn Ser Val Lys Glu Leu Thr Ser Ser Glu
                405                 410                 415

Asp Phe Thr Lys Lys Leu Glu Gly Glu His Ala Gln Leu Gly Ile Glu
            420                 425                 430

Asn Val Thr Ala Ala Glu Leu Glu Lys Leu Phe Lys Ala Val Glu Asn
        435                 440                 445

Leu Ala Lys Ala Ala Lys Glu Met Ala Pro Val Val Ala Glu Ser Pro
    450                 455                 460

Lys Lys Pro
465
```

<210> SEQ ID NO 5
<211> LENGTH: 823
<212> TYPE: PRT
<213> ORGANISM: Artificial Sequence
<220> FEATURE:
<223> OTHER INFORMATION: Synthetic chimeric antigenic polypeptide
      comprising OspC epitopes

<400> SEQUENCE: 5

Ser Glu Asp Phe Thr Asn Lys Leu Lys Asn Gly Asn Ala Gln Leu Gly
1               5                   10                  15

Leu Ala Ala Ala Thr Lys Gly Ala Lys Glu Leu Lys Asp Leu Ser Asp
            20                  25                  30

Ser Val Glu Ser Leu Val Lys Ala Ala Gln Val Met Leu Thr Asn Ser
        35                  40                  45

Ser Thr Gly Phe Thr Asn Lys Leu Lys Ser Gly His Ala Glu Leu Gly
    50                  55                  60

Pro Val Gly Gly Asn Ala Thr Lys Gly Ala Lys Glu Leu Lys Asp Leu
65                  70                  75                  80

Ser Glu Ser Val Glu Ala Leu Ala Lys Ala Ala Gln Ala Met Leu Thr
                85                  90                  95

Asn Ser Ser Glu Lys Phe Thr Lys Lys Leu Ser Glu Ser His Ala Asp
            100                 105                 110

Ile Gly Ile Gln Ala Ala Thr Lys Gly Ala Glu Glu Leu Asp Lys Leu
        115                 120                 125

Phe Lys Ala Val Glu Asn Leu Ser Lys Ser Thr Glu Phe Thr Asn Lys
    130                 135                 140

Leu Lys Ser Glu His Ala Val Leu Gly Leu Asp Asn Leu Thr Lys Gly
145                 150                 155                 160

Ala Ala Glu Leu Glu Lys Leu Phe Lys Ala Val Glu Asn Leu Ser Lys
                165                 170                 175

Ala Ala Gln Asp Thr Leu Lys Asn Ala Val Lys Glu Leu Thr Ser Pro
            180                 185                 190

Ile Val Ala Glu Ser Pro Lys Lys Pro Ser Glu Thr Phe Thr Asn Lys
        195                 200                 205

Leu Lys Glu Lys His Thr Asp Leu Gly Lys Glu Gly Val Thr Lys Gly
    210                 215                 220

Ala Glu Glu Leu Gly Lys Leu Phe Glu Ser Val Glu Val Leu Ser Lys
225                 230                 235                 240

Ala Ala Lys Glu Met Leu Ala Asn Ser Val Lys Glu Leu Thr Ser Ser
                245                 250                 255

Glu Glu Phe Ser Thr Lys Leu Lys Asp Asn His Ala Gln Leu Gly Ile
            260                 265                 270

Gln Gly Val Thr Lys Gly Val Glu Glu Leu Glu Lys Leu Ser Gly Ser
        275                 280                 285

Leu Glu Ser Leu Ser Ser Glu Asp Phe Thr Lys Lys Leu Glu Gly Glu
    290                 295                 300

His Ala Gln Leu Gly Ile Glu Asn Val Thr Ala Ala Glu Leu Glu Lys
305                 310                 315                 320

Leu Phe Lys Ala Val Glu Asn Leu Ala Lys Ala Ala Lys Glu Met Ala
                325                 330                 335

Lys Leu Lys Gly Glu His Thr Asp Leu Gly Lys Glu Gly Val Thr Lys
            340                 345                 350

Gly Ala Asp Glu Leu Glu Lys Leu Phe Glu Ser Val Lys Asn Leu Ser
        355                 360                 365

Lys Ala Ala Lys Glu Met Leu Thr Asn Ser Val Lys Glu Ser Glu Lys
    370                 375                 380

Phe Ala Gly Lys Leu Lys Asn Glu His Ala Ser Leu Gly Lys Lys Asp
385                 390                 395                 400

Ala Thr Lys Gly Ala Lys Glu Leu Lys Asp Leu Ser Asp Ser Val Glu

-continued

```
                405                 410                 415

Ser Leu Val Lys Ala Ser Asp Asp Phe Thr Lys Lys Leu Gln Ser Ser
            420                 425                 430

His Ala Gln Leu Gly Val Ala Gly Gly Ala Thr Thr Ala Asp Glu Leu
        435                 440                 445

Glu Lys Leu Phe Lys Ser Val Glu Ser Leu Ala Lys Ala Ala Gln Asp
    450                 455                 460

Ala Leu Ala Asn Ser Val Asn Glu Leu Thr Ser Lys Lys Leu Lys Glu
465                 470                 475                 480

Lys His Thr Asp Leu Gly Lys Lys Asp Ala Thr Ala Ala Glu Leu Glu
                485                 490                 495

Lys Leu Phe Glu Ser Val Glu Asn Leu Ala Lys Ala Ala Lys Glu Met
            500                 505                 510

Leu Ser Asn Ser Asn Lys Ala Phe Thr Asp Lys Leu Lys Ser Ser His
        515                 520                 525

Ala Glu Leu Gly Ile Ala Asn Gly Ala Ala Thr Lys Gly Ala Gln Glu
    530                 535                 540

Leu Glu Lys Leu Phe Glu Ser Val Lys Asn Leu Ser Lys Ala Ala Gln
545                 550                 555                 560

Glu Thr Leu Asn Asn Ser Val Lys Glu Ser Glu Ser Phe Thr Lys Lys
                565                 570                 575

Leu Ser Asp Asn Gln Ala Glu Leu Gly Ile Glu Asn Ala Thr Lys Gly
            580                 585                 590

Ala Glu Glu Leu Val Lys Leu Ser Glu Ser Val Ala Gly Leu Leu Lys
        595                 600                 605

Ala Ala Gln Ala Ile Leu Ala Asn Ser Val Lys Glu Leu Thr Ser Pro
    610                 615                 620

Val Val Ala Glu Ser Pro Lys Lys Pro Asn Asn Ser Gly Lys Asp Gly
625                 630                 635                 640

Asn Thr Ser Ala Asn Ser Ala Asp Glu Ser Val Lys Gly Pro Asn Leu
                645                 650                 655

Thr Glu Ile Ser Lys Lys Ile Thr Glu Ser Asn Ala Val Val Leu Ala
            660                 665                 670

Val Lys Glu Ile Glu Thr Leu Leu Ser Ser Ile Asp Glu Leu Ala Thr
        675                 680                 685

Lys Ala Ile Gly Gln Lys Ile Asp Ala Asn Gly Leu Gly Val Gln Ala
    690                 695                 700

Asn Gln Asn Gly Ser Leu Leu Ala Gly Ala Tyr Ala Ile Ser Thr Leu
705                 710                 715                 720

Ile Thr Gln Lys Leu Ser Ala Leu Asn Ser Glu Asp Leu Lys Glu Lys
                725                 730                 735

Val Ala Lys Val Lys Lys Cys Ser Glu Asp Phe Thr Asn Lys Leu Lys
            740                 745                 750

Asn Gly Asn Ala Gln Leu Gly Leu Ala Ala Ala Thr Asp Asp Asn Ala
        755                 760                 765

Lys Ala Ala Ile Leu Lys Thr Asn Gly Thr Asn Asp Lys Gly Ala Lys
    770                 775                 780

Glu Leu Lys Asp Leu Ser Asp Ser Val Glu Ser Leu Val Lys Ala Ala
785                 790                 795                 800

Gln Val Met Leu Thr Asn Ser Val Lys Glu Leu Thr Ser Pro Val Val
                805                 810                 815

Ala Glu Ser Pro Lys Lys Pro
            820
```

<210> SEQ ID NO 6
<211> LENGTH: 335
<212> TYPE: PRT
<213> ORGANISM: Artificial Sequence
<220> FEATURE:
<223> OTHER INFORMATION: Synthetic chimeric antigenic polypeptide comprising OspC epitopes

<400> SEQUENCE: 6

```
Ser Glu Asp Phe Thr Asn Lys Leu Lys Asn Gly Asn Ala Gln Leu Gly
1               5                   10                  15

Leu Ala Ala Ala Thr Lys Gly Ala Lys Glu Leu Lys Asp Leu Ser Asp
            20                  25                  30

Ser Val Glu Ser Leu Val Lys Ala Ala Gln Val Met Leu Thr Asn Ser
        35                  40                  45

Ser Thr Gly Phe Thr Asn Lys Leu Lys Ser Gly His Ala Glu Leu Gly
    50                  55                  60

Pro Val Gly Gly Asn Ala Thr Lys Gly Ala Lys Glu Leu Lys Asp Leu
65                  70                  75                  80

Ser Glu Ser Val Glu Ala Leu Ala Lys Ala Ala Gln Ala Met Leu Thr
                85                  90                  95

Asn Ser Ser Glu Lys Phe Thr Lys Lys Leu Ser Glu Ser His Ala Asp
            100                 105                 110

Ile Gly Ile Gln Ala Ala Thr Lys Gly Ala Glu Glu Leu Asp Lys Leu
        115                 120                 125

Phe Lys Ala Val Glu Asn Leu Ser Lys Ser Thr Glu Phe Thr Asn Lys
    130                 135                 140

Leu Lys Ser Glu His Ala Val Leu Gly Leu Asp Asn Leu Thr Lys Gly
145                 150                 155                 160

Ala Ala Glu Leu Glu Lys Leu Phe Lys Ala Val Glu Asn Leu Ser Lys
                165                 170                 175

Ala Ala Gln Asp Thr Leu Lys Asn Ala Val Lys Glu Leu Thr Ser Pro
            180                 185                 190

Ile Val Ala Glu Ser Pro Lys Lys Pro Ser Glu Thr Phe Thr Asn Lys
        195                 200                 205

Leu Lys Glu Lys His Thr Asp Leu Gly Lys Glu Gly Val Thr Lys Gly
    210                 215                 220

Ala Glu Glu Leu Gly Lys Leu Phe Glu Ser Val Glu Val Leu Ser Lys
225                 230                 235                 240

Ala Ala Lys Glu Met Leu Ala Asn Ser Val Lys Glu Leu Thr Ser Ser
                245                 250                 255

Glu Glu Phe Ser Thr Lys Leu Lys Asp Asn His Ala Gln Leu Gly Ile
            260                 265                 270

Gln Gly Val Thr Lys Gly Val Glu Glu Leu Glu Lys Leu Ser Gly Ser
        275                 280                 285

Leu Glu Ser Leu Ser Ser Glu Asp Phe Thr Lys Lys Leu Glu Gly Glu
    290                 295                 300

His Ala Gln Leu Gly Ile Glu Asn Val Thr Ala Ala Glu Leu Glu Lys
305                 310                 315                 320

Leu Phe Lys Ala Val Glu Asn Leu Ala Lys Ala Ala Lys Glu Met
                325                 330                 335
```

<210> SEQ ID NO 7
<211> LENGTH: 298
<212> TYPE: PRT

-continued

<213> ORGANISM: Artificial Sequence
<220> FEATURE:
<223> OTHER INFORMATION: Synthetic chimeric antigenic polypeptide
comprising OspC epitopes

<400> SEQUENCE: 7

Ala Lys Leu Lys Gly Glu His Thr Asp Leu Gly Lys Glu Gly Val Thr
1 5 10 15

Lys Gly Ala Asp Glu Leu Glu Lys Leu Phe Glu Ser Val Lys Asn Leu
20 25 30

Ser Lys Ala Ala Lys Glu Met Leu Thr Asn Ser Val Lys Glu Ser Glu
35 40 45

Lys Phe Ala Gly Lys Leu Lys Asn Glu His Ala Ser Leu Gly Lys Lys
50 55 60

Asp Ala Thr Lys Gly Ala Lys Glu Leu Lys Asp Leu Ser Asp Ser Val
65 70 75 80

Glu Ser Leu Val Lys Ala Ser Asp Asp Phe Thr Lys Lys Leu Gln Ser
85 90 95

Ser His Ala Gln Leu Gly Val Ala Gly Gly Ala Thr Thr Ala Asp Glu
100 105 110

Leu Glu Lys Leu Phe Lys Ser Val Glu Ser Leu Ala Lys Ala Ala Gln
115 120 125

Asp Ala Leu Ala Asn Ser Val Asn Glu Leu Thr Ser Lys Lys Leu Lys
130 135 140

Glu Lys His Thr Asp Leu Gly Lys Lys Asp Ala Thr Ala Ala Glu Leu
145 150 155 160

Glu Lys Leu Phe Glu Ser Val Glu Asn Leu Ala Lys Ala Ala Lys Glu
165 170 175

Met Leu Ser Asn Ser Asn Lys Ala Phe Thr Asp Lys Leu Lys Ser Ser
180 185 190

His Ala Glu Leu Gly Ile Ala Asn Gly Ala Ala Thr Lys Gly Ala Gln
195 200 205

Glu Leu Glu Lys Leu Phe Glu Ser Val Lys Asn Leu Ser Lys Ala Ala
210 215 220

Gln Glu Thr Leu Asn Asn Ser Val Lys Glu Ser Glu Ser Phe Thr Lys
225 230 235 240

Lys Leu Ser Asp Asn Gln Ala Glu Leu Gly Ile Glu Asn Ala Thr Lys
245 250 255

Gly Ala Glu Glu Leu Val Lys Leu Ser Glu Ser Val Ala Gly Leu Leu
260 265 270

Lys Ala Ala Gln Ala Ile Leu Ala Asn Ser Val Lys Glu Leu Thr Ser
275 280 285

Pro Val Val Ala Glu Ser Pro Lys Lys Pro
290 295

<210> SEQ ID NO 8
<211> LENGTH: 451
<212> TYPE: PRT
<213> ORGANISM: Artificial Sequence
<220> FEATURE:
<223> OTHER INFORMATION: Synthetic chimeric antigenic polypeptide
comprising OspC epitopes

<400> SEQUENCE: 8

Ala Lys Leu Lys Gly Glu His Thr Asp Leu Gly Lys Glu Gly Val Thr
1 5 10 15

Lys Gly Ala Asp Glu Leu Glu Lys Leu Phe Glu Ser Val Lys Asn Leu

-continued

```
            20                  25                  30

Ser Lys Ala Ala Lys Glu Met Leu Thr Asn Ser Val Lys Glu Ser Glu
        35                  40                  45

Lys Phe Ala Gly Lys Leu Lys Asn Glu His Ala Ser Leu Gly Lys Lys
    50                  55                  60

Asp Ala Thr Lys Gly Ala Lys Glu Leu Lys Asp Leu Ser Asp Ser Val
65                  70                  75                  80

Glu Ser Leu Val Lys Ala Ser Asp Asp Phe Thr Lys Lys Leu Gln Ser
                85                  90                  95

Ser His Ala Gln Leu Gly Val Ala Gly Gly Ala Thr Thr Ala Asp Glu
            100                 105                 110

Leu Glu Lys Leu Phe Lys Ser Val Glu Ser Leu Ala Lys Ala Ala Gln
        115                 120                 125

Asp Ala Leu Ala Asn Ser Val Asn Glu Leu Thr Ser Lys Lys Leu Lys
    130                 135                 140

Glu Lys His Thr Asp Leu Gly Lys Lys Asp Ala Thr Ala Ala Glu Leu
145                 150                 155                 160

Glu Lys Leu Phe Glu Ser Val Glu Asn Leu Ala Lys Ala Ala Lys Glu
                165                 170                 175

Met Leu Ser Asn Ser Asn Lys Ala Phe Thr Asp Lys Leu Lys Ser Ser
            180                 185                 190

His Ala Glu Leu Gly Ile Ala Asn Gly Ala Ala Thr Lys Gly Ala Gln
        195                 200                 205

Glu Leu Glu Lys Leu Phe Glu Ser Val Lys Asn Leu Ser Lys Ala Ala
    210                 215                 220

Gln Glu Thr Leu Asn Asn Ser Val Lys Glu Ser Glu Ser Phe Thr Lys
225                 230                 235                 240

Lys Leu Ser Asp Asn Gln Ala Glu Leu Gly Ile Glu Asn Ala Thr Lys
                245                 250                 255

Gly Ala Glu Glu Leu Val Lys Leu Ser Glu Ser Val Ala Gly Leu Leu
            260                 265                 270

Lys Ala Ala Gln Ala Ile Leu Ala Asn Ser Val Lys Glu Leu Thr Ser
        275                 280                 285

Pro Val Val Ala Glu Ser Pro Lys Lys Pro Ser Thr Glu Glu Lys Phe
    290                 295                 300

Asn Glu Lys Gly Glu Val Ser Glu Lys Ile Ile Thr Arg Ala Asp Gly
305                 310                 315                 320

Thr Arg Leu Glu Tyr Thr Gly Ile Lys Ser Asp Gly Ser Gly Lys Ala
                325                 330                 335

Lys Glu Val Leu Lys Gly Tyr Val Leu Glu Gly Thr Leu Thr Ala Glu
            340                 345                 350

Lys Thr Thr Leu Val Val Lys Glu Gly Thr Val Thr Leu Ser Lys Asn
        355                 360                 365

Ile Ser Lys Ser Gly Glu Val Ser Val Glu Leu Asn Asp Thr Asp Ser
    370                 375                 380

Ser Ala Ala Thr Lys Lys Thr Ala Ala Trp Asn Ser Gly Thr Ser Thr
385                 390                 395                 400

Leu Thr Ile Thr Val Asn Ser Lys Lys Thr Lys Asp Leu Val Phe Thr
                405                 410                 415

Lys Glu Asn Thr Ile Thr Val Gln Gln Tyr Asp Ser Asn Gly Thr Lys
            420                 425                 430

Leu Glu Gly Ser Ala Val Glu Ile Thr Lys Leu Asp Glu Ile Lys Asn
        435                 440                 445
```

Ala Leu Lys
    450

<210> SEQ ID NO 9
<211> LENGTH: 10
<212> TYPE: PRT
<213> ORGANISM: Artificial Sequence
<220> FEATURE:
<223> OTHER INFORMATION: Synthetic C-terminal domain peptide

<400> SEQUENCE: 9

Pro Val Val Ala Glu Ser Pro Lys Lys Pro
1               5                   10

<210> SEQ ID NO 10
<211> LENGTH: 158
<212> TYPE: PRT
<213> ORGANISM: Borrelia burgdorferi

<400> SEQUENCE: 10

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
    50                  55                  60

Gly His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155

<210> SEQ ID NO 11
<211> LENGTH: 158
<212> TYPE: PRT
<213> ORGANISM: Artificial Sequence
<220> FEATURE:
<223> OTHER INFORMATION: Snythetiec OspE mutant

<400> SEQUENCE: 11

Leu Ile Gly Ala Cys Lys Ile His Thr Ser Tyr Val Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Lys Ala Gly
    50                  55                  60

Gly His Ser Ala Thr Phe Phe Ser Leu Glu Glu Glu Glu Ile Asn Asn
65                  70                  75                  80

```
Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Val Lys Thr Lys Ile Glu Lys Ile Asn Asp Thr Glu Tyr Ile Thr
        115                 120                 125

Phe Leu Gly Asp Lys Ile Asn Asn Cys Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 12
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 12

Leu Ile Gly Ala Cys Lys Ile His Thr Ser Tyr Val Glu Gln Ser Asn
1               5                   10                  15

Gly Val Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Cys Leu Asn Ala Gly
    50                  55                  60

Gly His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 13
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 13

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
    50                  55                  60

Gly His Ser Ala Thr Phe Phe Ser Leu Glu Glu Glu Glu Ile Asn Asn
```

65 70 75 80

Phe Ile Lys Ala Ile Thr Glu Gly Gly Ser Phe Lys Thr Ser Leu Tyr
85 90 95

Tyr Gly Tyr Asn Asp Glu Glu Ser Asp Lys Asn Val Ile Lys Asn Lys
100 105 110

Glu Ile Lys Thr Lys Ile Glu Lys Ile Asn Asp Thr Glu Tyr Ile Thr
115 120 125

Phe Leu Gly Asp Lys Ile Asn Asn Ser Ala Gly Gly Asp Lys Ile Ala
130 135 140

Glu Tyr Ala Ile Ser Leu Glu Glu Leu Lys Arg Asn Leu Lys
145 150 155

<210> SEQ ID NO 14
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 14

Leu Ile Gly Ala Cys Lys Ile His Thr Ser Tyr Asp Glu Gln Ser Asn
1 5 10 15

Gly Glu Val Lys Val Lys Lys Ile Glu Phe Ser Glu Phe Thr Val Lys
20 25 30

Ile Lys Asn Lys Asn Asn Ser Asn Asn Trp Ala Asp Leu Gly Asp Leu
35 40 45

Val Val Arg Lys Glu Lys Asp Gly Ile Glu Thr Gly Leu Asn Ala Gly
50 55 60

Gly His Leu Ala Thr Phe Phe Ser Leu Glu Glu Glu Ile Asn Asn
65 70 75 80

Phe Ile Lys Ala Met Thr Glu Gly Gly Ser Phe Lys Thr Ser Leu Tyr
85 90 95

Tyr Gly Tyr Asn Asp Glu Glu Ser Asp Lys Asn Val Ile Lys Asn Lys
100 105 110

Glu Ile Lys Thr Lys Ile Glu Lys Ile Asn Asp Thr Glu Tyr Ile Thr
115 120 125

Phe Leu Gly Asp Lys Ile Asn Asn Ser Ala Gly Gly Asp Lys Ile Ala
130 135 140

Glu Tyr Ala Ile Ser Leu Glu Glu Leu Lys Arg Asn Leu Lys
145 150 155

<210> SEQ ID NO 15
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 15

Leu Ile Gly Ala Cys Lys Ile His Thr Ser Tyr Asp Glu Gln Ser Asn
1 5 10 15

Gly Glu Val Lys Val Lys Lys Ile Glu Phe Ser Glu Phe Thr Val Lys
20 25 30

Ile Lys Asn Lys Asn Asn Ser Asn Asn Trp Ala Asp Leu Arg Asp Leu
35 40 45

Val Val Arg Lys Glu Lys Asp Gly Ile Glu Thr Gly Leu Asn Ala Gly
50 55 60

-continued

```
Gly His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 16
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 16

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
    50                  55                  60

Gly His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Val Arg Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 17
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 17

Leu Ile Gly Ala Cys Lys Ile His Thr Ser Tyr Asp Glu Gln Ser Asn
1               5                   10                  15

Gly Glu Val Lys Val Glu Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Lys Ala Gly
    50                  55                  60
```

```
Gly His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 18
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 18

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Gln Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
    50                  55                  60

Ala His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Val Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 19
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 19

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
```

```
    50                  55                  60

Gly His Ser Ala Thr Phe Phe Ser Leu Glu Glu Glu Glu Ile Asn Asn
65                  70                  75                  80

Phe Ile Lys Ala Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Val Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Val
    130                 135                 140

Glu Tyr Ala Ile Ser Leu Glu Glu Leu Lys Arg Asn Leu Lys
145                 150                 155


<210> SEQ ID NO 20
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 20

Leu Ile Gly Ala Cys Lys Ile His Pro Ser Tyr Asp Glu Gln Ser Asn
1               5                   10                  15

Gly Glu Val Lys Ile Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
    50                  55                  60

Gly His Ser Thr Thr Phe Phe Ser Leu Glu Glu Glu Glu Ile Asn Asn
65                  70                  75                  80

Phe Ile Lys Pro Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Val Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 21
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 21

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45
```

```
Val Val Arg Lys Glu Lys Asp Gly Ile Glu Thr Gly Leu Asn Ala Gly
    50                  55                  60

Gly His Ser Ala Thr Phe Phe Ser Leu Glu Glu Glu Ile Asn Asn
65                  70                  75                  80

Phe Ile Asn Pro Met Thr Glu Gly Gly Ser Phe Lys Thr Ser Leu Tyr
                85                  90                  95

Tyr Arg Tyr Asn Asp Glu Glu Ser Asp Lys Ser Val Ile Lys Asn Lys
            100                 105                 110

Glu Met Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 22
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 22

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Asn
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Arg Gly Leu Asn Ala Gly
    50                  55                  60

Gly His Ser Ala Thr Phe Phe Ser Leu Glu Glu Glu Glu Ile Asn Asn
65                  70                  75                  80

Phe Ile Lys Pro Met Thr Glu Gly Gly Ser Phe Lys Thr Ser Leu Tyr
                85                  90                  95

Tyr Gly Tyr Asn Asp Glu Glu Ser Asp Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Ser Asn Leu Lys
145                 150                 155


<210> SEQ ID NO 23
<211> LENGTH: 145
<212> TYPE: PRT
<213> ORGANISM: Artificial Sequence
<220> FEATURE:
<223> OTHER INFORMATION: Synthetic OspE mutant

<400> SEQUENCE: 23

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45
```

```
Val Val Arg Lys Glu Lys Asp Gly Ile Glu Thr Gly Leu Asn Ala Gly
    50                  55                  60

Gly His Ser Ala Thr Phe Phe Ser Leu Glu Glu Glu Glu Ile Asn Asn
65                  70                  75                  80

Phe Ile Lys Pro Met Thr Glu Asp Gly Ser Phe Lys Thr Ser Leu Tyr
                85                  90                  95

Tyr Gly Tyr Asn Asp Glu Glu Ser Asp Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu
145


<210> SEQ ID NO 24
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 24

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Ile Val Lys
            20                  25                  30

Ile Lys Asn Lys Asn Asn Ser Asn Asn Cys Ala Asp Leu Gly Asp Leu
        35                  40                  45

Val Val Arg Lys Glu Lys Asp Gly Ile Glu Thr Gly Leu Asn Ala Gly
    50                  55                  60

Gly His Ser Ala Thr Phe Val Ser Leu Glu Glu Glu Glu Ile Asn Asn
65                  70                  75                  80

Phe Ile Lys Pro Met Thr Glu Gly Gly Ser Phe Lys Thr Ser Leu Tyr
                85                  90                  95

Tyr Gly Tyr Asn Asp Glu Glu Ser Asp Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 25
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 25

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Glu Gly Asp Leu
```

```
        35                  40                  45

Val Ile Arg Lys Glu Lys Asp Gly Ile Glu Thr Gly Leu Asn Ala Gly
    50                  55                  60

Arg His Ser Ala Thr Phe Phe Ser Leu Glu Glu Glu Glu Ile Asn Asn
65                  70                  75                  80

Phe Ile Lys Pro Met Thr Glu Gly Gly Ser Phe Lys Thr Ser Leu Tyr
                85                  90                  95

Tyr Gly Tyr Asn Asp Glu Glu Ser Asp Lys Ser Val Ile Lys Asn Lys
            100                 105                 110

Glu Val Lys Thr Lys Ile Glu Lys Ile Asn Asp Thr Glu Tyr Ile Thr
        115                 120                 125

Phe Leu Gly Asp Lys Ile Asn Asn Ser Ala Gly Arg Asp Lys Ile Ala
    130                 135                 140

Glu Tyr Thr Ile Ser Leu Glu Glu Leu Lys Arg Asn Leu Lys
145                 150                 155


<210> SEQ ID NO 26
<211> LENGTH: 158
<212> TYPE: PRT
<213> ORGANISM: Artificial Sequence
<220> FEATURE:
<223> OTHER INFORMATION: Synthetic OspE mutant

<400> SEQUENCE: 26

Leu Ile Gly Ala Cys Lys Ile His Thr Ser Tyr Asp Glu Gln Ser Asn
1               5                   10                  15

Gly Glu Val Lys Val Lys Lys Ile Glu Phe Ser Glu Phe Thr Val Lys
            20                  25                  30

Ile Lys Asn Lys Asn Asn Ser Asn Asn Trp Ala Asp Leu Gly Asp Leu
        35                  40                  45

Val Val Arg Lys Glu Lys Asp Gly Ile Glu Thr Gly Leu Asn Ala Gly
    50                  55                  60

Gly Gln Leu Ala Thr Phe Leu Ser Leu Glu Glu Glu Glu Ile Asn Asn
65                  70                  75                  80

Phe Ile Lys Pro Met Thr Glu Gly Gly Ser Phe Lys Thr Ser Leu Tyr
                85                  90                  95

Tyr Gly Tyr Asn Asp Glu Glu Ser Gly Lys Asn Val Ile Lys Asn Lys
            100                 105                 110

Glu Ile Lys Thr Lys Ile Glu Lys Ile Asn Asp Thr Glu Tyr Ile Thr
        115                 120                 125

Phe Leu Gly Asp Lys Ile Asn Asn Ser Ala Gly Gly Asp Lys Ile Ala
    130                 135                 140

Glu Tyr Ala Ile Ser Leu Glu Glu Leu Lys Arg Asn Leu Lys
145                 150                 155


<210> SEQ ID NO 27
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 27

Leu Ile Gly Ala Cys Lys Ile His Thr Ser Tyr Asp Glu Gln Ser Ser
1               5                   10                  15

Gly Glu Ile Asn His Thr Leu Tyr Asp Glu Gln Ser Asn Gly Glu Leu
            20                  25                  30
```

```
Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asp Thr Gly Leu Asn Ala Gly Gly His Ser
65                  70                  75                  80

Ala Thr Phe Phe Ser Leu Lys Glu Ser Glu Val Asn Asn Phe Ile Lys
                85                  90                  95

Ala Met Thr Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Asp Lys Ile Asn Asn Gly Val Gly Gly Asp Lys Thr Ala Glu Tyr Ala
145                 150                 155                 160

Ile Pro Leu Glu Val Leu Lys Lys Asn Leu Lys
                165                 170


<210> SEQ ID NO 28
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 28

Leu Ile Gly Ala Cys Lys Ile His Thr Ser Tyr Asp Glu Gln Ser Ser
1               5                   10                  15

Gly Glu Ile Asn His Thr Leu Tyr Asp Glu Gln Ser Asn Gly Glu Leu
            20                  25                  30

Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asp Thr Gly Leu Asp Ala Gly Gly His Ser
65                  70                  75                  80

Ala Thr Phe Phe Ser Leu Lys Glu Ser Glu Val Asn Asn Phe Ile Lys
                85                  90                  95

Ala Met Thr Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Val Gly Ala Glu His Ile Ala Phe Leu Gly
    130                 135                 140

Asp Lys Ile Asn Asn Gly Val Gly Gly Asp Lys Thr Ala Glu Tyr Val
145                 150                 155                 160

Ile Pro Leu Glu Val Val Lys Lys Asn Leu Lys
                165                 170


<210> SEQ ID NO 29
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 29
```

```
Leu Ile Gly Ala Cys Lys Ile His Thr Ser Tyr Asp Glu Gln Ser Ser
1               5                   10                  15

Gly Glu Ile Asn His Thr Leu Tyr Asp Glu Gln Ser Asn Gly Glu Leu
            20                  25                  30

Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asn Thr Gly Leu Asn Ala Gly Gly His Ser
65                  70                  75                  80

Asp Met Phe Phe Ser Leu Lys Glu Ser Glu Val Asn Asn Phe Ile Lys
                85                  90                  95

Ala Met Thr Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Val Leu Gly
    130                 135                 140

Asp Lys Ile Asn Asn Gly Val Gly Gly Asp Lys Thr Ala Glu Tyr Ala
145                 150                 155                 160

Ile Pro Leu Glu Val Leu Lys Lys Asn Leu Lys
                165                 170
```

<210> SEQ ID NO 30
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 30

```
Leu Ile Gly Ala Cys Lys Ile His Thr Ser Tyr Asp Glu Gln Ser Ser
1               5                   10                  15

Val Glu Ile Asn His Thr Leu Tyr Asp Glu Gln Ser Asn Gly Glu Leu
            20                  25                  30

Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asp Thr Gly Leu Asn Ala Gly Glu His Ser
65                  70                  75                  80

Ala Thr Phe Phe Ser Leu Lys Glu Ser Glu Val Asn Asn Phe Ile Lys
                85                  90                  95

Ala Met Ser Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Asp Lys Ile Asn Asn Gly Val Gly Gly Asp Lys Thr Ala Glu Tyr Ala
145                 150                 155                 160

Ile Pro Leu Glu Val Leu Lys Lys Asn Leu Lys
                165                 170
```

<210> SEQ ID NO 31

-continued

<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 31

```
Leu Ile Gly Ala Cys Lys Ile His Thr Ser Tyr Gly Glu Gln Ser Ser
1               5                   10                  15

Gly Glu Ile Asn His Thr Leu Tyr Asp Glu Gln Ser Asn Gly Asp Leu
            20                  25                  30

Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asp Thr Ser Leu Asn Ala Gly Gly His Ser
65                  70                  75                  80

Ala Thr Phe Phe Ser Leu Lys Glu Ser Glu Val Asn Asn Phe Ile Lys
                85                  90                  95

Ala Met Thr Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Asp Lys Ile Asn Asn Ser Val Gly Gly Asp Lys Thr Ala Glu Tyr Ala
145                 150                 155                 160

Ile Pro Leu Glu Val Leu Lys Lys Asn Leu Lys
                165                 170
```

<210> SEQ ID NO 32
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 32

```
Leu Ile Gly Ala Cys Lys Ile His Thr Ser Tyr Asp Glu Gln Ile Ser
1               5                   10                  15

Gly Glu Ile Asn Arg Thr Leu Tyr Asp Glu Gln Ser Asn Gly Glu Leu
            20                  25                  30

Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asp Thr Gly Leu Asn Ala Gly Gly His Ser
65                  70                  75                  80

Ala Thr Phe Phe Ser Leu Thr Glu Ser Glu Val Asn Asn Phe Ile Lys
                85                  90                  95

Thr Met Thr Lys Gly Gly Ser Phe Lys Thr Ser Leu Tyr Phe Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Asp Lys Ile Asn Asn Gly Val Gly Gly Asp Lys Thr Ala Glu Tyr Ala
```

```
145                 150                 155                 160

Ile Pro Ile Glu Val Leu Lys Lys Asn Leu Lys
                165                 170


<210> SEQ ID NO 33
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 33

Leu Ile Gly Ala Cys Lys Ile His Thr Ser Tyr Gly Glu Gln Ser Ser
1               5                   10                  15

Gly Glu Ile Asn His Thr Leu Tyr Asp Glu Gln Ser Asn Gly Glu Leu
            20                  25                  30

Lys Leu Lys Lys Ile Glu Phe Ser Lys Ile Thr Val Lys Ile Lys Asn
        35                  40                  45

Lys Asp Lys Asn Ser Asn Trp Thr Asp Leu Gly Asp Leu Val Val Arg
    50                  55                  60

Lys Glu Glu Asn Gly Ile Asp Thr Gly Leu Asn Ala Gly Gly His Ser
65                  70                  75                  80

Val Thr Phe Phe Ser Leu Lys Glu Ser Gly Val Asn Asn Phe Ile Lys
                85                  90                  95

Ala Met Thr Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Asp Lys Ile Asn Asn Gly Val Gly Gly Asp Lys Thr Ala Glu Tyr Ala
145                 150                 155                 160

Val Pro Leu Glu Val Leu Lys Lys Asn Leu Lys
                165                 170


<210> SEQ ID NO 34
<211> LENGTH: 171
<212> TYPE: PRT
<213> ORGANISM: Artificial Sequence
<220> FEATURE:
<223> OTHER INFORMATION: Synthetic OspE mutant

<400> SEQUENCE: 34

Leu Ile Gly Ala Cys Lys Ile His Thr Ser Tyr Asp Glu Gln Ser Ser
1               5                   10                  15

Gly Glu Ile Asn His Thr Leu Tyr Asp Glu Gln Ser Asn Gly Glu Leu
            20                  25                  30

Lys Leu Lys Lys Ile Glu Phe Ser Lys Phe Thr Val Lys Ile Lys Asn
        35                  40                  45

Lys Thr Val Asn Ser Asn Trp Thr Asp Leu Gly Asp Leu Val Val Arg
    50                  55                  60

Lys Glu Glu Asn Gly Ile Asp Thr Gly Leu Asn Ala Gly Gly His Ser
65                  70                  75                  80

Ala Thr Phe Phe Ser Leu Lys Glu Ser Glu Val Asn Asn Phe Ile Lys
                85                  90                  95

Ala Met Thr Lys Gly Gly Ser Phe Lys Thr Ser Leu Tyr Tyr Gly Tyr
            100                 105                 110
```

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Val Asn Ile Asn Asn Gly Val Gly Gly Asp Lys Thr Ala Glu Tyr Ala
145                 150                 155                 160

Ile Pro Leu Glu Val Leu Lys Lys Asn Leu Lys
                165                 170

<210> SEQ ID NO 35
<211> LENGTH: 162
<212> TYPE: PRT
<213> ORGANISM: Artificial Sequence
<220> FEATURE:
<223> OTHER INFORMATION: Synthetic OspE mutant

<400> SEQUENCE: 35

Ser Ile Gly Ala Cys Lys Ile His Thr Ser Tyr Asp Glu Gln Ser Ser
1               5                   10                  15

Gly Glu Ile Asn His Thr Leu Tyr Asp Glu Gln Ser Asn Gly Glu Leu
            20                  25                  30

Lys Leu Lys Lys Ile Glu Phe Ser Lys Phe Thr Val Lys Ile Lys Asn
        35                  40                  45

Lys Asp Asn Asn Ser Asn Trp Thr Asp Leu Gly Asp Leu Val Val Arg
    50                  55                  60

Lys Glu Glu Asn Gly Ile Asp Thr Gly Leu Asn Ala Gly Gly His Ser
65                  70                  75                  80

Ala Thr Phe Phe Ser Leu Lys Glu Ser Glu Val Asn Asn Phe Ile Lys
                85                  90                  95

Ala Met Thr Lys Gly Gly Ser Phe Lys Thr Ser Leu Tyr Tyr Gly Tyr
            100                 105                 110

Lys Tyr Glu Gln Ser Ser Ala Asn Gly Ile Gln Asn Lys Glu Ile Ile
        115                 120                 125

Thr Lys Ile Glu Ser Ile Asn Gly Ala Glu His Ile Ala Phe Leu Gly
    130                 135                 140

Asp Lys Leu Asn Thr Val Trp Gly Lys Ile Lys Gln Leu Asn Met Gln
145                 150                 155                 160

Tyr His

<210> SEQ ID NO 36
<211> LENGTH: 210
<212> TYPE: PRT
<213> ORGANISM: Borrelia burgdorferi

<400> SEQUENCE: 36

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

-continued

```
Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro
    210
```